United States Patent
Fox

(10) Patent No.: US 6,887,695 B2
(45) Date of Patent: May 3, 2005

(54) TRANSGLUTAMINASE ZTG2

(75) Inventor: Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 43 days.

(21) Appl. No.: 10/109,084

(22) Filed: Mar. 27, 2002

(65) Prior Publication Data

US 2003/0054526 A1 Mar. 20, 2003

Related U.S. Application Data

(60) Provisional application No. 60/279,289, filed on Mar. 28, 2001.

(51) Int. Cl.$^7$ .............................. C12N 9/10; C12P 21/06
(52) U.S. Cl. ..................................... 435/193; 435/69.1
(58) Field of Search ................................ 435/193, 69.1; 536/23.2; 530/387.3

(56) References Cited

FOREIGN PATENT DOCUMENTS

| WO | WO 0222830 A2 | * | 3/2002 |
| WO | WO 02/26950 A2 | * | 4/2002 |
| WO | WO 02/059265 A2 | | 8/2002 |

OTHER PUBLICATIONS

Grenard P. et al. Evolution of transglutaminase Genes; Identification of a Transglutaminase Gene Cluster on Human Chromosome 15q15, J. Biol. Chem. 2001, 276, 33066–33078.*

International Protein Index, IP100044409, European Bioinformatics Institute, Jan. 8, 2002.

* cited by examiner

Primary Examiner—Rebecca E. Prouty
Assistant Examiner—Malgorzata A. Walicka
(74) Attorney, Agent, or Firm—Gary E. Parker

(57) ABSTRACT

Transglutaminase polypeptides, polynucleotides encoding them, methods of making them, and methods of using them are disclosed. The polypeptides comprise residues 1-X of SEQ ID NO:2, wherein X is an integer from 462 to 704, inclusive. The compositions and methods of the invention may be used for a variety of purposes in industry, research, and medicine.

2 Claims, 1 Drawing Sheet

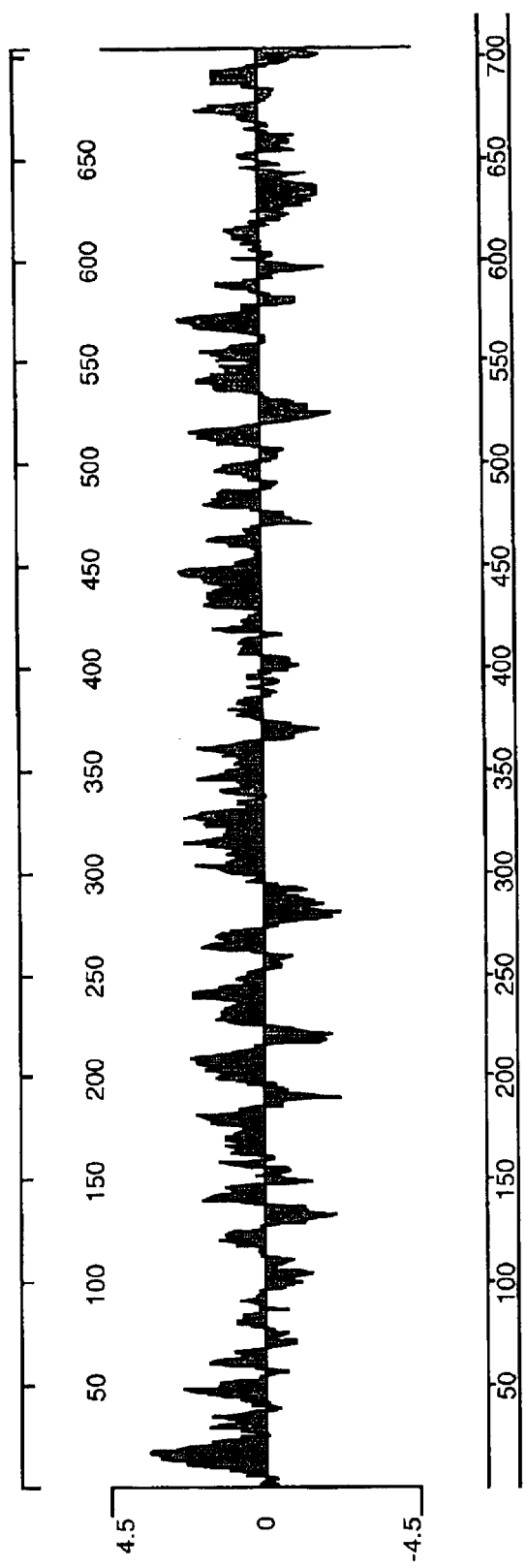

TRANSGLUTAMINASE ZTG2

CROSS-REFERENCE TO RELATED APPLICATION

This application claims priority under 35 U.S.C. § 119(e) from provisional application No. 60/279,289, filed Mar. 28, 2001.

BACKGROUND OF THE INVENTION

Transglutaminases are a group of calcium-dependent enzymes that catalyze the formation of ε-(γ-glutaminyl) lysine isopeptide bonds between protein-bound glutamine and lysine residues. These bonds are responsible for the crosslinking of large proteins and the incorporation of small primary amines into proteins. Transglutaminases are believed to be widely distributed in nature, since these crosslinks are found in both prokaryotic and eukaryotic cells. See generally, Folk, *Ann. Rev. Biochem.* 49:517–531, 1980.

Transglutaminase-catalyzed protein crosslinking reactions have been implicated in both normal and pathological processes in mammalian cells and tissues. The crosslink may act to maintain some forms of protein structure, such as in the terminal differentiation of epidermal cell layers and in other cellular architecture. An intracellular transglutaminase known as epidermal or Type I transglutaminase has been isolated and cloned from rabbit epithelial cells (Floyd and Jetten, *Mol. Cell. Biol.* 9:4846–4851, 1989), and a transglutaminase has been isolated and cloned from guinea pig liver cells (Ikura et al., *Biochem.* 27:2898–2905, 1988). Other transglutaminases include hair follicle transglutaminase, keratinocyte transglutaminase, prostate transglutaminase (Wilson et al., *Fed. Proc.* 38:1809, 1979), various microbial transglutaminases (U.S. Pat. Nos. 5,156,956 and 5,252,469), transglutaminase H (U.S. Pat. No. 5,726,051), and $TG_x$ (Aeschlimann et al., *J. Biol. Chem.* 273:3452–3460, 1998). Lee et al. (*Prep. Biochem.* 16:321–335, 1986) have described the purification of a transglutaminase from human erythrocytes. These transglutaminases have been shown to be distinct from a plasma transglutaminase, factor XIII, which stabilizes fibrin clots. DNAs encoding human and bovine factor XIII have been cloned and sequenced. See, Ichinose et al., *Biochem.* 25:6900–6906, 1986; Takahashi et al., *Proc. Natl. Acad. Sci. USA* 83:8018–8023, 1986; WIPO Publication WO 96/21025.

Transglutaminases have been employed for crosslinking purposes in a variety of fields. Certain microbial transglutaminases have found use in the food processing industry for enhancing the texture of processed foods, particularly cheese and fish products. See, for example, U.S. Pat. No. 6,100,053. Others have been used in enzyme-catalyzed fluorescent labeling of proteins, in the introduction of cleavable crosslinks, and in the solid-phase, reversible removal of specific proteins from biological systems. Factor XIII has been proposed for a variety of therapeutic uses, including treatment of subarachnoid hemorrhage (e.g., Thie et al., *Neurochirurgia* 34:107–110, 1991), neonatal intracranial hemorrhage (Shirahata et al., *Thrombosis Res.* 57:755–763, 1990), inflammatory bowel disease (Lorenz et al., *Haemostasis* 21:5–9, 1991), and postoperative bleeding (U.S. Pat. No. 5,607,917; Laohaprasit et al., *Neurosurgery* 32:630–633, 1993; Shainoff et al., *J. Thorac. Carciovasc. Surg.* 108:437–445, 1994), and as an immunosuppressant (U.S. Pat. No. 5,464,615).

DISCLOSURE OF THE INVENTION

Within one aspect the present invention provides an isolated polypeptide comprising residues 1-X of SEQ ID NO:2, wherein X is an integer from 462 to 704, inclusive. Within one embodiment the polypeptide is from 462 to 2000 amino acid residues in length. Within other embodiments the polypeptide is from 462 to 1,800 residues in length. Within a further embodiment the polypeptide comprises residues 1 through 704 of SEQ ID NO:2. Within an additional embodiment the polypeptide consists of residues 1 through 704 of SEQ ID NO:2. Within another embodiment the polypeptide further comprises an affinity tag.

Within a second aspect of the invention there is provided an isolated polypeptide comprising residues 1 through 462 of SEQ ID NO:2, wherein the polypeptide is not more than 800 amino acid residues in length.

Within a third aspect of the invention there is provided an isolated polypeptide comprising residues 1-X of SEQ ID NO:2, wherein X is an integer from 462 to 704, inclusive, and wherein the polypeptide is not more than 800 amino acid residues in length.

Within a fourth aspect of the invention there is provided an expression vector comprising the following operably linked elements: (a) a transcription promoter; (b) a DNA segment encoding a polypeptide comprising residues 1-X of SEQ ID NO:2, wherein X is an integer from 462 to 704, inclusive; and (c) a transcription terminator. Within one embodiment the expression vector further comprises a secretory signal sequence operably linked to the DNA segment. Within other embodiments the polypeptide is from 462 to 1,800 residues in length. Within another embodiment the polypeptide comprises residues 1 through 704 of SEQ ID NO:2. Within a further embodiment the polypeptide consists of residues 1 through 704 of SEQ ID NO:2. Within an additional embodiment the polypeptide further comprises an affinity tag.

Within a fifth aspect of the invention there is provided a cultured cell containing an expression vector as disclosed above, wherein the cell expresses the DNA segment.

Within a sixth aspect of the invention there is provided a method of making a polypeptide comprising the steps of culturing a cell as disclosed above under conditions whereby the DNA segment is expressed, and recovering the polypeptide encoded by the DNA segment. Within one embodiment the expression vector further comprises a secretory signal sequence operably linked to the DNA segment and the polypeptide is secreted into and recovered from a culture medium in which the cell is cultured.

Within a seventh aspect of the invention there is provided a polypeptide produced by one of the methods disclosed above.

Within an eighth aspect of the invention there is provided an antibody that specifically binds to a polypeptide as disclosed above.

Within a ninth aspect of the invention there is provided a method of forming an ε-(γ-glutaminyl) lysine isopeptide bond between first and second polypeptides. The method comprises incubating the first and second polypeptides in the presence of a third polypeptide having transglutaminase activity, wherein the third polypeptide comprises amino acid residues 1 through 462 of SEQ ID NO:2.

Within a tenth aspect of the invention there is provided an isolated polynucleotide encoding amino acid residues 1 through X of SEQ ID NO:2, wherein X is an interger from 462 through 704, inclusive. Within certain embodiments the isolated polynucleotide is a polynucleotide as shown in SEQ ID NO:1 or SEQ ID NO:3.

These and other aspects of the invention will become evident upon reference to the following detailed description and the attached drawing.

The drawing is a Kyte-Doolittle hydrophilicity plot of the polypeptide of SEQ ID NO:2. The drawing was prepared using Protean™ 3.14 (DNAStar, Madison, Wis.).

The term "affinity tag" is used herein to denote a polypeptide segment that can be attached to a second polypeptide to provide for purification or detection of the second polypeptide or provide sites for attachment of the second polypeptide to a substrate. In principal, any polypeptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Glu-Tyr-Met-Pro-Met-Glu; SEQ ID NO:5) (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "complement" of a polynucleotide molecule is a polynucleotide molecule having a complementary base sequence and reverse orientation as compared to a reference sequence. For example, the sequence 5' ATGCACGGG 3' is complementary to 5' CCCGTGCAT 3'.

"Conservative amino acid substitutions" are defined by the BLOSUM62 scoring matrix of Henikoff and Henikoff, *Proc. Natl. Acad. Sci. USA* 89:10915–10919, 1992, an amino acid substitution matrix derived from about 2,000 local multiple alignments of protein sequence segments, representing highly conserved regions of more than 500 groups of related proteins. As used herein, the term "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least one 1 (e.g., 1, 2 or 3), while more preferred conservative amino acid substitutions are characterized by a BLOSUM62 value of at least 2 (e.g., 2 or 3).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. The isolated polypeptide or protein may be prepared substantially free of other polypeptides or proteins, particularly those of animal origin. For some purposes, the polypeptides and proteins will be prepared in a highly purified form, i.e. greater than 95% pure or greater than 99% pure. When used in this context, the term "isolated" does not exclude the presence of the same polypeptide or protein in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide, protein, or polynucleotide obtained from one species that is the functional counterpart of a polynucleotide, polypeptide, or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. Thus, a protein "consisting of," for example, from 15 to 1500 amino acid residues may further contain one or more carbohydrate chains.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides, in part, a novel transglutaminase referred to herein as "ztg2". The ztg2 polypeptide sequence shown in SEQ ID NO:2 comprises 704 amino acid residues. This sequence is truncated at its amino terminus. The full-length ztg2 protein includes six additional N-terminal amino acid residues, however it is believed that these additional amino acid residues are not required for enzymatic activity. The full-length ztg2 DNA and amino acid sequences are shown in SEQ ID NO:6 and SEQ ID NO:7, respectively. Those skilled in the art will recognize that more residues may be present in some forms of the protein (e.g., alternatively spliced forms).

Ztg2 was identified by its similarity to previously known transglutaminases, including $TG_x$ (Aeschlimann et al., ibid.).

The human ztg2 gene shown in SEQ ID NO:3 includes 12 exons. At least one additional exon is believed to exist 5' of SEQ ID NO:3.

The ztg2 protein shown in SEQ ID NO:2 includes structural features that are conserved among the known transglutaminases. The active site residues are Cys273, His332, and Asp355. A His residue corresponding to the conserved Tyr/His near the active site of transglutaminases is located at residue 532 of SEQ ID NO:2, and a conserved Trp residue believed to be important for biological activity is located at residue 237 of SEQ ID NO:2. Residues 395–397 and 444–449 correspond to conserved sequences in calcium binding domains of other transglutaminases.

The ztg2 sequence shown in SEQ ID NO:2 comprises four large structural domains: a beta sandwich, comprising residues 1–141; a catalytic core, comprising residues 142–462; beta barrel 1, comprising residues 483–599; and beta barrel 2, comprising residues 600–704. Those skilled in the art will recognize that domain boundaries are somewhat imprecise and may vary by ±5 residues.

While not wishing to be bound by theory, it is believed that ztg2, like most tranglutaminases, does not comprise a pro-peptide, and proteolytic processing is not believed to be required for catalytic activity. All elements required for such activity are believed to reside within residues 1–462 of SEQ ID NO:2. The present invention thus includes proteins comprising residues 1-X of SEQ ID NO:2, wherein X is an integer from 462 to 704, inclusive. Within certain embodiments of the invention, X is 462, 467, 472, 482, 487, 500, 550, 600, 650, 700, or 704.

Amino acid substitutions can be made within the ztg2 sequence so long as the active site residues and calcium binding domain are retained and the higher order structure is not disrupted. The significant degree of sequence similarity among known transglutaminases provides additional guidance in the selection of amino acid substitutions.

Polypeptides of the present invention can be prepared with one or more amino acid substitutions, deletions or additions as compared to SEQ ID NO:2. These changes can be of a minor nature, that is conservative amino acid substitutions and other changes that do not significantly affect the folding or activity of the protein or polypeptide, and include amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20–25 residues, or an affinity tag as disclosed above. Two or more affinity tags may be used in combination. Polypeptides comprising affinity tags can further comprise a polypeptide linker and/or a proteolytic cleavage site between the ztg2 polypeptide and the affinity tag. Exemplary cleavage sites include, without limitation, thrombin cleavage sites and factor Xa cleavage sites.

The polypeptides of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

The present invention further provides a variety of other polypeptide fusions and related multimeric proteins comprising one or more polypeptide fusions. For example, a ztg2 polypeptide can be prepared as a fusion to a multimerizing protein as disclosed in U.S. Pat. Nos. 5,155,027 and 5,567,584. Exemplary multimerizing proteins in this regard include immunoglobulin constant region domains. For example, a ztg2 polypeptide can be joined to an IgG Fc fragment (consisting essentially of $C_H2$, $C_H3$, and hinge). Such fusions are typically secreted as multimeric molecules wherein the Fc portions are disulfide-bonded to each other and two non-Ig polypeptides are arrayed in close proximity to each other. Dimerization can also be stabilized by fusing a ztg2 polypeptide to a leucine zipper sequence (Riley et al., *Protein Eng.* 9:223–230, 1996; Mohamed et al., *J. Steroid Biochem. Mol. Biol.* 51:241–250, 1994). Immunoglobulin-ztg2 polypeptide fusions and leucine zipper fusions can be expressed in genetically engineered cells to produce a variety of multimeric ztg2 analogs. Auxiliary domains can be fused to ztg2 polypeptides to target them to specific cells, tissues, or macromolecules (e.g., collagen). For example, a ztg2 polypeptide or protein can be targeted to a predetermined cell type by fusing a ztg2 polypeptide to a ligand that specifically binds to a receptor on the surface of the target cell. In this way, polypeptides and proteins can be targeted for therapeutic or diagnostic purposes. A ztg2 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996. Within immunoglobulin-ztg2 fusion proteins, certain amino acid subsititutions can be introduced into the Ig portion to alter effector functions associated with the native Ig. For example, amino acid substitutions can be made at EU index positions 234, 235, and 237 to reduce binding to FCγRI, and at EU index positions 330 and 331 to reduce complement fixation. See, Duncan et al., *Nature* 332:563–564, 1988; Winter et al., U.S. Pat. No. 5,624,821; Tao et al., *J. Exp. Med.* 178:661, 1993; and Canfield and Morrison, *J. Exp. Med.* 173:1483, 1991. The carboxyl-terminal lysine residue can be removed from the $C_H3$ domain to increase homogeneity of the product. Within fusions to an Ig heavy chain polypeptide, the Cys residue within the hinge region that is ordinarily disulfide-bonded to the light chain can be replaced with another amino acid residue, such as a serine residue, if the Ig fusion is not co-expressed with a light chain polypeptide. However, an Ig-ztg2 fusion polypeptide can be co-expressed with a wild-type or fused light chain polypeptide as disclosed in U.S. Pat. No. 6,018,026.

Ztg2 polypeptide fusions will generally contain not more than about 2,000 amino acid residues, usually not more than about 1,800 residues, often not more than about 1,500 residues, more often not more than about 1,200 residues, and will in many cases be considerably smaller (e.g., up 1000 residues, up to 800 residues, up to 750 residues, or up to 725 residues in length). For example, a ztg2 polypeptide of 704 residues (residues 1–704 of SEQ ID NO:2) can be fused to *E. coli* β-galactosidase (1,021 residues; see Casadaban et al., *J. Bacteriol.* 143:971–980, 1980), a 10-residue spacer, and a 4-residue factor Xa cleavage site to yield a polypeptide of 1,739 residues. In a second example, residues 1–462 of SEQ ID NO:2 are fused to maltose binding protein (approximately 370 residues), a 4-residue cleavage site, and a 6-residue polyhistidine tag. In a third example, residues 1 to 704 of SEQ ID NO:2 are fused at the C terminus to an IgG Fc fragment of 232 residues and at the N terminus to a secretory peptide of 20–25 residues.

Amino acid sequence changes are made in ztg2 polypeptides so as to minimize disruption of higher order structure essential to biological activity. As noted above, conservative amino acid changes are generally less likely to negate activity than are non-conservative changes. Changes in amino acid residues will be made so as not to disrupt the higher-order structure that is characteristic of the transglutaminase family. See, Aeschlimann et al., ibid. Conserved motifs will also be maintained. The effects of amino acid sequence changes can be predicted by computer modeling using available software (e.g., the Insight II® viewer and homology modeling tools; MSI, San Diego, Calif.) or determined by analysis of crystal structure (see, e.g., Lapthorn et al, *Nature* 369:455–461, 1994; Lapthorn et al., *Nat. Struct. Biol.* 2:266–268, 1995). Essential amino acids in the polypeptides of the present invention can be identified experimentally according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced throughout the molecule, and the resultant mutant molecules are tested for biological activity as disclosed below to identify amino acid residues that are critical to the activity of the molecule. Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988). A hydrophilicity profile of SEQ ID NO:2 is shown in the Figure. Those skilled in the art will recognize that this hydrophilicity will be taken into account when designing alterations in the amino acid sequence of a ztg2 polypeptide, so as not to disrupt the overall profile.

The present invention further provides polynucleotide molecules, including DNA and RNA molecules, encoding ztg2 polypeptides. These polynucleotides include the sense strand; the anti-sense strand; and the DNA as double-stranded, having both the sense and anti-sense strand annealed together by hydrogen bonds. A representative DNA sequence encoding a human ztg2 protein is set forth in SEQ ID NO:1. DNA sequences encoding other ztg2 proteins can be readily generated by those of ordinary skill in the art based on the genetic code. Counterpart RNA sequences can be generated by substitution of U for T. Polynucleotides encoding ztg2 proteins and complementary polynucleotides are useful in the production of ztg2 proteins and for diagnostic and investigatory purposes.

Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the ztg2 polypeptide of SEQ ID NO:2. Those skilled in the art will recognize that the degenerate sequence of SEQ ID NO:4 also provides all RNA sequences encoding SEQ ID NO:2 by substituting U for T. Thus, ztg2 polypeptide-encoding polynucleotides comprising nucleotides 1 to X of SEQ ID NO:4, wherein X is an integer from 1386 to 2112, inclusive, and their respective RNA equivalents are contemplated by the present invention. Table 1 sets forth the one-letter codes used within SEQ ID NO:4 to denote degenerate nucleotide positions. "Resolutions" are the nucleotides denoted by a code letter. "Complement" indicates the code for the complementary nucleotide (s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | I |
| Pro | P | CCA CCC CCG CCT | CCN |

TABLE 2-continued

| Amino Acid | One Letter Code | Codons | Degenerate Codon |
|---|---|---|---|
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences shown in SEQ ID NO:2. Variant sequences can be readily tested for functionality as described herein.

One of ordinary skill in the art will also appreciate that different species can exhibit preferential codon usage. See, in general, Grantham et al., *Nuc. Acids Res.* 8:1893–1912, 1980; Haas et al. *Curr. Biol.* 6:315–324, 1996; Wain-Hobson et al., *Gene* 13:355–364, 1981; Grosjean and Fiers, *Gene* 18:199–209, 1982; Holm, *Nuc. Acids Res.* 14:3075–3087, 1986; and Ikemura, *J. Mol. Biol.* 158:573–597, 1982. "Preferential codon usage" is a term of art referring to the bias in codon usage within the genomes of certain species, whereby certain protein translation codons are more frequently used, thus favoring one or a few representatives of the possible codons encoding each amino acid (see Table 2). For example, the amino acid threonine (Thr) can be encoded by ACA, ACC, ACG, or ACT, but in mammalian cells ACC is the most commonly used codon. In other species, for example, insect cells, yeast, viruses or bacteria, different Thr codons may be preferred. Preferred codons for a particular species can be introduced into the polynucleotides of the present invention by a variety of methods known in the art. Introduction of preferred codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferred codons can be tested and optimized for expression in various host cell species, and tested for functionality as disclosed herein.

It is preferred that ztg2 polynucleotides hybridize to similarly sized regions of SEQ ID NO: 1, or a sequence complementary thereto, under stringent conditions. In general, stringent conditions are selected to be about 5° C. lower than the thermal melting point I for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, ztg2-encoding polynucleotides include DNA and RNA. Methods for preparing DNA and RNA are well known in the art. In general, RNA is isolated from a tissue or cell that produces large amounts of ztg2 RNA, including testis, lung, and B-cells. Such tissues and cells are identified by conventional procedures, such as Northern blotting (Thomas, *Proc. Natl. Acad. Sci. USA* 77:5201, 1980). Total RNA can be prepared using guanidine-HCI extraction followed by isolation by centrifugation in a CsCl gradient (Chirgwin et al., *Biochemistry* 18:52–94, 1979). Poly (A)⁺RNA is prepared from total RNA using the method of Aviv and Leder (*Proc. Natl. Acad. Sci. USA* 69:1408–12, 1972). Complementary DNA (cDNA) is prepared from poly(A)⁺RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequence disclosed herein, or parts thereof, for probing or priming a library. Polynucleotides encoding ztg2 polypeptides are identified and isolated by, for example, hybridization or polymerase chain reaction ("PCR", Mullis, U.S. Pat. No. 4,683,202). Expression libraries can be probed with antibodies to ztg2, receptor fragments, or other specific binding partners.

The polynucleotides of the present invention can also be synthesized using automated equipment ("gene machines"). The current method of choice is the phosphoramidite method. If chemically synthesized, double-stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. Gene synthesis methods are well known in the art. See, for example, Glick and Pasternak, *Molecular Biotechnology, Principles & Applications of Recombinant DNA*, ASM Press, Washington, D.C., 1994; Itakura et al., *Annu. Rev. Biochem.* 53: 323–356, 1984; and Climie et al., *Proc. Natl. Acad. Sci. USA* 87:633–637, 1990.

The ztg2 polynucleotide sequences disclosed herein can be used to isolate counterpart polynucleotides from other species (orthologs). These orthologous polynucleotides can be used, inter alia, to prepare the respective orthologous proteins. These other species include, but are not limited to, mammalian, avian, amphibian, reptile, fish, insect and other vertebrate and invertebrate species. Of particular interest are ztg2 polynucleotides and polypeptides from other mammalian species, including murine, porcine, ovine, bovine, canine, feline, equine, and other primate polypeptides. Orthologs of human ztg2 can be cloned using information and compositions provided by the present invention in combination with conventional cloning techniques. For example, a cDNA can be cloned using mRNA obtained from a tissue or cell type that expresses ztg2 as disclosed above. A ztg2-encoding cDNA can then be isolated by a variety of methods, such as by probing with a complete or partial human cDNA or with one or more sets of degenerate probes based on the disclosed sequences, or by PCR using primers designed from the representative human ztg2 sequence disclosed herein. Within an additional method, a cDNA library can be used to transform or transfect host cells, and expression of the cDNA of interest can be detected with an antibody to ztg2 polypeptide. Similar techniques can also be applied to the isolation of genomic clones.

Those skilled in the art will recognize that the sequence disclosed in SEQ ID NO:1 represents a single allele of human ztg2 and that natural variation, including allelic variation and alternative splicing, is expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs that retain the catalytic activity of ztg2 are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

For any ztg2 polypeptide, including variants and fusion proteins, one of ordinary skill in the art can readily generate a fully degenerate polynucleotide sequence encoding that variant using the information set forth in Tables 1 and 2, above.

Conserved regions of ztg2, identified by alignment with sequences of other transglutaminase family members, can be used to identify related polynucleotides and proteins. For instance, reverse transcription-polymerase chain reaction (RT-PCR) and other techniques known in the art can be used to amplify sequences encoding the conserved motifs present in ztg2 from RNA obtained from a variety of tissue sources.

Ztg2 polynucleotide sequences disclosed herein can also be used as probes or primers to clone 5' non-coding regions of a ztg2 gene, including promoter sequences. These flanking sequences can be used to direct the expression of ztg2 and other recombinant proteins. In addition, 5' flanking sequences can be used as targeting sites for regulatory constructs to activate or increase expression of endogenous ztg2 genes as disclosed by Treco et al., U.S. Pat. No. 5,641,670.

The polypeptides of the present invention, including full-length polypeptides, biologically active or immunogenic fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells, including cultured cells of multicellular organisms. Techniques for manipulating cloned DNA molecules and introducing exogenous DNA into a variety of host cells are disclosed by Sambrook et al.,

*Molecular Cloning: A Laboratory Manual*, 2$^{nd}$ ed., Cold Spring Harbor Laboratory Press, Cold Spring Harbor, N.Y., 1989, and Ausubel et al., eds., *Current Protocols in Molecular Biology*, Green and Wiley and Sons, N.Y., 1993.

In general, a DNA sequence encoding a ztg2 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors, and other elements is a matter of routine design within the level of ordinary skill in the art. Many such elements are described in the literature and are available through commercial suppliers.

To direct a ztg2 polypeptide into the secretory pathway of a host cell, a secretory signal sequence (also known as a leader sequence, prepro sequence or pre sequence) is provided in the expression vector. The secretory signal sequence may be derived from a secreted protein (e.g., t-PA; see, U.S. Pat. No. 5,641,655) or synthesized de novo. The secretory signal sequence is operably linked to the ztg2 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al.,*J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, 10801 University Blvd., Manassas, Va. USA under accession numbers 98669 and 98668, respectively, as well as derivatives of these vectors.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47–58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566–4579, 1993). This system, which utilizes transfer vectors, is commercially available in kit form (Bacto-Bac™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a ztg2-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses ztg2 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, in general, Glick and Pasternak, *Molecular Biotechnology: Principles and Applications of*

Recombinant DNA, ASM Press, Washington, D.C., 1994. See also, U.S. Pat. No. 5,300,435. Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075; and Bishop et al., U.S. Pat. No. 5,612,456. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986; Cregg, U.S. Pat. No. 4,882,279; and Raymond et al., *Yeast* 14, 11–23, 1998. Production of recombinant proteins in *Pichia methanolica* is disclosed in U.S. Pat. Nos. 5,716,808, 5,736,383, 5,854,039, and 5,888,768. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a ztg2 polypeptide in bacteria such as *E. coli*, the polypeptide may be retained in the cytoplasm or may be directed to the periplasmic space by a bacterial secretion sequence. In the former case, the cells are lysed, and the ztg2 polypeptide is recovered from the lysate. If the polypeptide is present in the cytoplasm as insoluble granules, the cells are lysed, and the granules are recovered and denatured using, for example, guanidine isothiocyanate or urea. The denatured polypeptide can then be refolded by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. Liquid cultures are provided with sufficient aeration by conventional means, such as shaking of small flasks or sparging of fermentors.

Ztg2 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* ($2^{nd}$ edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Depending upon the intended use, the polypeptides and proteins of the present invention can be purified to $\geq 80\%$ purity, $\geq 90\%$ purity, $\geq 95\%$ purity, or to a pharmaceutically pure state, that is greater than 99.9% pure with respect to contaminating macromolecules, particularly other proteins and nucleic acids, and free of infectious and pyrogenic agents.

Ztg2 polypeptides (including fusion polypeptides) can be purified using fractionation and/or conventional purification methods and media, such as by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, N.Y., 1994. Proteins comprising a polyhistidine affinity tag (typically about 6 histidine residues) are purified by affinity chromatography on a nickel or cobalt chelate resin. See, for example, Houchuli et al., *Bio/Technol.* 6: 1321–1325, 1988. Proteins comprising a Glu-Glu tag can be purified by immunoaffinity chromatography according to conventional procedures. See, for example, Grussenmeyer et al., ibid. Maltose binding protein fusions are purified on an amylose column according to methods known in the art.

Using methods known in the art, ztg2 proteins can be prepared glycosylated or non-glycosylated, PEGylated or non-PEGylated, and may or may not include an initial methionine amino acid residue. The actual structure of a recombinant protein will depend in part on the chosen host cell due to, for example, post translational processing or proteolysis.

Ztg2 proteins, including variants of wild-type ztg2, are tested for activity in conventional transglutaminase activity assays, a variety of which are known in the art. Such assays include incorporation of $^3$H-putrescine into casein (Griffiths et al., *J. Invest. Dermatol.* 96:620 (Abstract 534), 1991), incorporation of $^{14}$C-putrescine into dimethyl casein (Lorand et al., *Biochem.* 50:623, 1972), and incorporation of dansyl cadaverine into casein (Buxman and Wuepper, *Biochim. Biophys. Acta* 452:356–369, 1976; Lorand and Gotoh, *Methods Enzymol.* 19:770–782, 1970).

Ztg2 proteins can be tested in animal models of disease, including models of impaired wound healing; models of impaired hemostasis, including perioperative bleeding and subarachnoid hemorrhage; models of inflammatory processes, including psoriasis and inflammatory bowel disease; and models of autoimmune disorders, including multiple sclerosis, diabetes, and scleroderma. Suitable models are known in the art. For example, animal models of psoriasis include the analysis of histological alterations in adult mouse tail epidermis (Hofbauer et al, Brit. *J. Dermatol.* 118:85–89, 1988; Bladon et al., *Arch Dermatol. Res.* 277:121–125, 1985). In this model, anti-psoriatic activity is indicated by the induction of a granular layer and orthokeratosis in areas of scale between the hinges of the tail epidermis. Typically, a topical ointment is applied daily for seven consecutive days, then the animal is sacrificed, and tail skin is examined histologically. An additional model is provided by grafting psoriatic human skin to congenitally athymic (nude) mice (Krueger et al., *J. Invest. Dermatol.* 64:307–312, 1975). Such grafts have been shown to retain the characteristic histology for up to eleven weeks. As in the mouse tail model, the test composition is applied to the skin at predetermined intervals for a period of one to several weeks, at which time the animals are sacrificed and the skin grafts examined histologically. A third model has been disclosed by Fretland et al. (*Inflammation* 14:727–739, 1990). Briefly, inflammation is induced in guinea pig epidermis by topically applying phorbol ester (phorbol-12-myristate-13-acetate; PMA), typically at ca. 2 mg/ml in acetone, or the calcium ionophore A23187, typically at 200 nmol in 0.1 ml DMSO, to one ear and vehicle to the contralateral ear. Test compounds are applied concurrently with the pro-inflammatory agent. Histological analysis is performed at 96 hours after induction of inflammation. This model duplicates many symptoms of human psoriasis, including edema, inflammatory cell diapedesis and infiltration, high LTB$_4$ levels, and epidermal proliferation. Cerebral ischemia can be studied in a rat model as disclosed by Relton et al. (*Exp. Neurol.* 138:206–213, 1996) and Loddick et al. (*Biochem. Biophys. Res. Comm.* 234:211–215, 1997). Wound-healing models include the linear skin incision model of Mustoe et al. (*Science* 237:1333, 1987). In a typical procedure, a 6-cm incision is made in the dorsal pelt of an adult rat, then closed with wound clips. Test substances and controls (in, e.g., solution, gel, or powder form) are applied before primary closure. It is preferred to limit administration to a single application, although additional applications can be made on succeeding days by careful injection at several sites under the incision. Wound breaking strength is evaluated between 3 and 21 days after wounding. In a second model, multiple, small, full-thickness excisions are made on the ear of a rabbit. The cartilage in the ear splints the wound, removing the variable of wound contraction from the evaluation of closure. Experimental treatments and controls are applied. The geometry and anatomy of the wound site allow for reliable quantification of cell ingrowth and epithelial migration, as well as quantitative analysis of the biochemistry of the wounds (e.g., collagen content). See, Mustoe et al., *J. Clin. Invest.* 87:694, 1991. The rabbit ear model can be modified to create an ischemic wound environment, which more closely resembles the clinical situation (Ahn et al., *Ann. Plast. Surg.* 24:17, 1990). Within a third model, healing of partial-thickness skin wounds in pigs or guinea pigs is evaluated (LeGrand et al., *Growth Factors* 8:307, 1993). Experimental treatments are applied daily on or under dressings. Seven days after wounding, granulation tissue thickness is determined. This model is suitable for dose-response studies, as it is more quantitative than other in vivo models of wound healing. A full thickness excision model can also be employed. Within this model, the epidermis and dermis are removed down to the panniculus carnosum in rodents or the subcutaneous fat in pigs. Experimental treatments are applied topically on or under a dressing, and can be applied daily if desired. The wound closes by a combination of contraction and cell ingrowth and proliferation. Measurable endpoints include time to wound closure, histologic score, and biochemical parameters of wound tissue. Impaired wound healing models are also known in the art (e.g., Cromack et al., *Surgery* 113:36, 1993; Pierce et al., *Proc. Natl. Acad. Sci. USA* 86:2229, 1989; Greenhalgh et al., *Amer. J. Pathol.* 136:1235, 1990). Delay or prolongation of the wound healing process can be induced pharmacologically by treatment with steroids, irradiation of the wound site, or by concomitant disease states (e.g., diabetes). Linear incisions or full-thickness excisions are most commonly used as the experimental wound. Endpoints are as disclosed above for each type of wound. Subcutaneous implants can be used to assess compounds acting in the early stages of wound healing (Broadley et al., *Lab. Invest.* 61:571, 1985; Sprugel et al., *Amer. J. Pathol.* 129: 601, 1987). Implants are prepared in a porous, relatively non-inflammatory container (e.g., polyethylene sponges or expanded polytetrafluoroethylene implants filled with bovine collagen) and placed subcutaneously in mice or rats. The interior of the implant is empty of cells, producing a "wound space" that is well-defined and separable from the preexisting tissue. This arrangement allows the assessment of cell influx and cell type as well as the measurement of vasculogenesis/angiogenesis and extracellular matrix production.

Additional models will be evident to those skilled in the art based on the range of diseases that have been associated with deficiencies or other imbalances in transglutaminases or that have been shown to be responsive to treatment with transglutaminases. Ztg2 proteins can be delivered to test animals by injection, infusion, or topical application, or can be produced in vivo by way of, for example, viral or naked DNA delivery systems or transgenic expression.

Expression of ztg2 polynucleotides and inhibitory polynucleotides in animals provides models for study of the biological effects of overproduction or inhibition of protein activity in viva. Polynucleotides can be introduced into test animals, such as mice, using viral vectors or naked DNA, or transgenic animals can be produced. Viral and other suitable delivery systems are disclosed in more detail below.

Exemplary viral delivery systems include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994; and Douglas and Curiel, *Science & Medicine* 4:44–53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection. By deleting portions of the adenovirus genome, larger inserts (up to 7 kb) of heterologous DNA can be accommodated. These inserts can be incorporated into the viral DNA by direct ligation or by homologous recombination with a co-transfected plasmid. When intravenously administered to intact animals, adenovirus primarily targets the liver. If the adenoviral delivery system has an E1 gene deletion, the virus cannot replicate in the host cells unless the E1 gene is provided by the host cell (e.g., the human 293 cell line). However, the host's tissue (e.g., liver) will express and process (and, if a signal sequence is present, secrete) the heterologous protein. Retroviral vectors can be used as described, for example, by Anderson et al., U.S. Pat. No. 5,399,346; Mann et al., Cell 33:153, 1983; Temin et al., U.S. Pat. No. 4,650,764; Temin et al., U.S. Pat. No. 4,980,289; Markowitz et al., J. Virol. 62:1120, 1988; Temin et al., U.S. Pat. No. 5,124,263; Dougherty et al., WIPO publication WO 95/07358; and Kuo et al., Blood 82:845, 1993.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., J. Biol. Chem. 263:14621–14624, 1988; Wu et al., J. Biol. Chem. 267:963–967, 1992; and Johnston and Tang, Meth. Cell Biol. 43:353–365, 1994.

In another method, the vector can be introduced by "lipofection" in vivo using liposomes. Synthetic cationic lipids can be used to prepare liposomes for in vivo transfection (Felgner et al., Proc. Natl. Acad. Sci. USA 84:7413–7417, 1987; Mackey et al., Proc. Natl. Acad. Sci. USA 85:8027–8031, 1988). The use of lipofection to introduce exogenous genes into specific organs in vivo has certain practical advantages, including molecular targeting of liposomes to specific cells. Directing transfection to particular cell types is particularly advantageous in tissues with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Transgenic mice, engineered to express a ztg2 gene, and mice that exhibit a complete absence of ztg2 gene function, referred to as "knockout mice" (Snouwaert et al., Science 257:1083, 1992), can be generated (Lowell et al., Nature 366:740–742, 1993). These mice are employed to study the ztg2 gene and the encoded protein in an in vivo system. Transgenic mice are particularly useful for investigating the role of ztg2 proteins in early development because they allow the identification of developmental abnormalities or blocks resulting from the over- or underexpression of a specific factor.

The ztg2 polypeptides are contemplated for use in the treatment or prevention of conditions associated with deficiencies or other imbalances in transglutaminases or that have been shown to be responsive to treatment with transglutaminases. Such conditions include, but are not limited to, immunological disorders, including autoimmune diseases and inflammatory disorders; impaired wound healing; bleeding disorders, including intraventricular hemorrhage, subarachnoid hemorrhage, and perioperative blood loss (including blood loss associated with cardiopulmonary bypass); and unstable angina. Polypeptides can be administered to patients or produced in vivo using gene therapy techniques as generally disclosed herein.

Ztg2 polypeptides may be used as components of a fibrin-based tissue glue. Tissue glues of this type are known in the art and generally comprise a transglutaminase and fibrinogen. The ztg2 and fibrinogen will ordinarily be formulated as a liquid or gel. Prior to or during application to a site of tissue damage, the ztg2/fibrinogen mixture is combined with thrombin to convert the fibrinogen to fibrin. The ztg2/fibrinogen and thrombin components can be packaged in a multi-compartment syringe or spray applicator, a variety of which are known in the art. See, in general, U.S. Pat. Nos. 4,414,976 and 4,909,251.

Ztg2 polypeptides may be used to promote healing of wounds. Ztg2 polypeptides can be applied directly to wounds as aqueous or lipid-based fromulations, or can be incorporated into wound dressings. Such formulations can also comprise one or more additional therapeutic agents, such as an antibiotic or a growth factor, such as PDGF. See, U.S. Pat. No. 4,889,919.

Ztg2 polypeptides may also be used as a substitute for factor XIII in the treatment of bleeding disorders. For example, ztg2 polypeptides may be used in the treatment of ulcerative colitis as generally disclosed for factor XIII in U.S. Pat. No. 5,378,687. The use of factor XIII in the prevention of intraventricular hemorrhage and subarachnoid hemorrhage is disclosed in U.S. Pat. No. 5,114,916. Reduction of perioperative blood loss is disclosed in WIPO Publication WO 93/12813. Reduction of delayed bleeding of wounds or post-operative hemorrhage is disclosed in WIPO Publication WO 94/11022.

Ztg2 polypeptides may be used in the treatment of vascular implants, grafts, stents, and the like to reduce thrombogenicity and increase vessel patency as generally disclosed in U.S. Pat. Nos. 5,324,647 and 5,693,098.

The ztg2 proteins of the present invention may be combined with other therapeutic agents to augment the activity (e.g., wound-healing activity) of such agents. For example, a ztg2 protein may be used in combination with a growth factor to promote the healing of chronic wounds in diabetic patients.

Doses of ztg2 polypeptides will vary according to the severity of the condition being treated and overall patient condition, and may range from approximately 10 µg/kg to 10 mg/kg body weight, usually 100 µg/kg to 5 mg/kg, more often 100 µg/kg to 1 mg/kg. Actual doses will be determined by the particular condition to be treated, route of administration, patient traits, and other factors that will be evident to the skilled practitioner. Larger doses may be used in life-threatening or other severe conditions. For pharmaceutical use, ztg2 polypeptides are formulated in a pharmaceutically acceptable carrier or vehicle in a form suitable for topical, enteral, or parenteral administration. Routes of administration include, without limitation, injection (including intravenous, intramuscular, and subcutaneous), infusion, topical, nasal, and rectal. Suitable aqueous vehicles include water, buffered water, saline, 0.3% glycine, glucose solutions, mannitol solutions, and the like. In the alternative, the polypeptide may be packaged as a lyophilized powder, optionally in combination with a pre-measured diluent, and resuspended immediately prior to use. Topical delivery vehicles include both lipidic and aqueous formulations including, for example, gels, creams, and ointments. The use of aqueous, polymeric gels for the delivery of pharmaceutical proteins is disclosed by, for example, Finkenaur et al., U.S. Pat. No. 5,427,778; Edwards et al., U.S. Pat. No. 5,770,228; and Finkenaur et al., U.S. Pat. No. 4,717,717; and Cini et al., U.S. Pat. No. 5,457,093. Gels comprise biocompatible, water soluble or water swellable polymers that form viscous solutions in water. Such polymers include, without limitation, polysaccharides, including methyl cellulose, hydroxypropyl cellulose, hydroxypropylmethyl cellulose, hydroxyethyl cellulose, dextrans, starch, chitosan, and alginic acid; glycosaminoglycans, including hyaluronic acid, chondroitin, chondroitin sulfates, heparin, and heparan sulfate; proteins, including collagen, gelatin, and fibronectin; and acrylamides, including polyacrylamide and polymethacrylamide. Gels are generally prepared with a viscosity of from 200 cps to 100,000 cps, more commonly about 1000 cps to 30,000 cps at room temperature, the latter range corresponding to about 0.25–10% hydroxyethyl cellulose in water. Higher viscosity gels are known in the art (e.g., Finkenaur et al., U.S. Pat. No. 5,427,778). Viscosity can be adjusted by varying the concentration and/or length of the component polymer(s). Gels are prepared by combining the polymer with a suitable buffer, such as a low ionic strength citrate, phosphate, or acetate buffer at neutral or slightly acidic pH. A preservative (antimicrobial agent) such as methyl paraben, propyl paraben, benzyl alcohol, or the like, will generally be included. Following thorough mixing, the solution is sterilized by suitable means (e.g., autoclaving). The mixture is cooled, and filter-sterilized ztg2 protein is added.

Solid carriers include biodegradable sponges, blocks, flosses, and the like composed of, for example, gelatin, collagen, cellulose, or chitin. Such materials are known in the art. See, for example, Correll, U.S. Pat. No. 2,465,357; Miyata et al., U.S. Pat. No. 4,271,070; and Munck et al., WO 90/13320. For example, a solution of ztg2 and, optionally, one or more additional therapeutic agents is injected into a sponge, and the sponge is air-dried at a temperature of 30–100° C. for a time sufficient to reduce the water content to below 50%, preferably below 10%. Aqueous or lipidic formulations may be applied to or incorporated into wound dressings. Pharmaceutical compositions may further include one or more bulking agents, excipients, preservatives, solubilizers, buffering agents, albumin or other protein to prevent protein loss on vial surfaces, amino acids, polyalcohols, surface active agents, salts, etc. Formulation methods are within the level of ordinary skill in the art. See, *Remington: The Science and Practice of Pharmacy*, Gennaro, ed., Mack Publishing Co., Easton, Pa., $19^{th\ ed.}$, 1995.

One or more additional components may be added to a formulation of ztg2 protein to increase its effectiveness. Such additional components include, without limitation, calcium ions, protease inhibitors (e.g., aprotinin), fibrinogen, prostaglandins, coagulation factors, antihistimines, vasopressins, growth factors, vitamins, antibiotics, and the like.

Gene therapy provides an alternative therapeutic approach for delivery of ztg2 polypeptides. If a mammal has a mutated or absent ztg2 gene, a polynucleotide encoding a ztg2 polypeptide can be introduced into the cells of the mammal. Suitable viral and other delivery systems are disclosed above.

Ztg2 polypeptides can also be used to prepare antibodies that specifically bind to ztg2 polypeptides. As used herein, the term "antibodies" includes polyclonal antibodies, monoclonal antibodies, antigen-binding fragments thereof such as $F(ab')_2$ and Fab fragments, single chain antibodies, and the like, including genetically engineered antibodies. Non-human antibodies can be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Alternative techniques for generating or selecting antibodies useful herein include in vitro exposure of lymphocytes to a ztg2 protein, and selection of antibody display libraries in phage or similar vectors (for instance, through use of immobilized or labeled ztg2 polypeptide). Antibodies are defined to be specifically binding if they bind to a ztg2 protein with an affinity at least 10-fold greater than the binding affinity to a control (non-ztg2) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The affinity of a monoclonal antibody can be readily determined by one of ordinary skill in the art (see, for example, Scatchard, *Ann. NY Acad. Sci.* 51:660–672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a ztg2 polypeptide may be increased through the use of an adjuvant such as alum (aluminum hydroxide) or Freund's complete or incomplete adjuvant. Polypeptides useful for immunization also include fusion polypeptides, such as fusions of a ztg2 polypeptide or a portion thereof with an immunoglobulin polypeptide (see, in general, WIPO Publication WO 96/20718) or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

The present invention thus provides polypeptides that comprise an epitope-bearing portion of a protein as shown in SEQ ID NO:2. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short, synthetic polypeptides that mimic part of a protein sequence are routinely capable of eliciting an antiserum that reacts with the partially mimicked protein. See, Sutcliffe et al.,

*Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979). Anti-peptide antibodies are not conformation-dependent and can be used to detect proteins in fragmented or otherwise altered forms (Niman et al., *Proc. Natl. Acad. Sci. USA* 82:7924–7928, 1985), such as might occur in body fluids or cell culture media. Antibodies to short polypeptides may also recognize proteins in native conformation and will thus be useful for monitoring protein expression and protein isolation, and in detecting ztg2 proteins in solution, such as by ELISA or in immunoprecipitation studies.

Antigenic, epitope-bearing polypeptides of the present invention are useful for raising antibodies, including monoclonal antibodies, that specifically bind to a ztg2 polypeptide. Although antigenic, epitope-bearing polypeptides can contain as few as six amino acid residues, within the present invention such polypeptides will ordinarily comprise at least 15 contiguous amino acid residues of SEQ ID NO:2, typically from 15 to about 30 contiguous amino acid residues of SEQ ID NO:2, and may comprise a larger portion of SEQ ID NO:2, e.g., at least 30, 50, 100, 150, 200, 250, 300, 350, 400, 450, 500, 550, 600, 650, or 700 residues or up to the entire sequence of ztg2. It is preferred that the amino acid sequence of the epitope-bearing polypeptide is selected to provide substantial solubility in aqueous solvents, that is the sequence includes relatively hydrophilic residues, and hydrophobic residues are substantially avoided. Such regions of SEQ ID NO:2 include, for example, residues 10–15, 44–50, 58–63, 202–212, 226–231, 237–243, 301–307, 312–317, 323–328, 356–362, 442–448, 476–481, 508–513, 512–517, and 670–676. Exemplary longer polypeptide immunogens include those comprising residues 226–246, 301–328, and 418–449. Polypeptides can be prepared with an additional N-terminal or C-terminal Cys residue to facilitate coupling.

A variety of assays known to those skilled in the art can be utilized to detect antibodies that specifically bind to a ztg2 polypeptide. Exemplary assays are described in detail in *Antibodies: A Laboratory Manual*, Harlow and Lane (Eds.), Cold Spring Harbor Laboratory Press, 1988. Representative examples of such assays include concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to ztg2 may be used for affinity purification of ztg2 proteins; within diagnostic assays for determining circulating levels of ztg2 proteins; for detecting or quantitating soluble ztg2 protein as a marker of underlying pathology or disease; for immunolocalization within whole animals or tissue sections, including immunodiagnostic applications; for immunohistochemistry; for screening expression libraries; and for other uses that will be evident to those skilled in the art. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates.

Ztg2 polypeptides may be used in the laboratory for cross linking proteins, including the production of cross-linked gels and matrices. Ztg2 can also be used as a reference standard within assays for transglutaminase activity.

The ztg2 polypeptides of the present invention can also be used in the preparation of food materials, such as paste food, cheese, and the like, and can be added to dehydrated fish to prevent deterioration caused by protozoans, e.g., myxamoeba. Ztg2 polypeptides can also be used in the preparation of ground meat of okiomi (*Euphasia superba*) by adding to dehydrated meat parts from 0.1 to 100 units, usually about 1–40 units per gram of protein to improve meat texture and quality. Frozen granular meats can be improved by combining meat material with a ztg2 polypeptide at 1–500 units per gram of meat protein at 30–60° C. for 10–120 minutes to promote crosslinking between glutamine and lysine residues contained in meat preparations. Other food-related uses include the improvement of baking quality of flour and modification of food taste and texture.

Other uses of ztg2 polypeptides include use in the enzyme-catalyzed labeling of proteins and cell membranes (Iwanij, *Eur. J. Biochem.* 80:359–368, 1977), in the introduction of cleavable crosslinks, in the solid-phase reversible removal of specific proteins from biological systems, and in leather processing.

For industrial and laboratory use, ztg2 polypeptides can be formulated as dry or liquid preparations. Dry preparations include powders and granulates, the latter including non-dusting granulates. See, for example, U.S. Pat. Nos. 4,106,991 and 4,661,452. Liquid preparations will generally be aqueous solutions and may contain one or more stabilizers or preservatives that are compatible with the intended use. Suitable stabilizers include, without limitation, sugars, polyols, and organic acids.

Ztg2 expression can be used as a marker for screening for agonists and antagonists of cellular apoptosis. Identifying agents that inhibit the expresion of ztg2 within a cell provides a means to prevent or delay atrophic changes characteristic of many degenerative changes, particularly degenerative nerve diseases such as Parkinson's disease and Alzheimer's disease. Inhibition of apoptosis may also enhance blood cell counts in chemotherapy patients. Ztg2 polypeptides or ztg2-encoding polynucleotides can also be used to identify agents that induce apoptotic activity in a cell. Such agents may be used, for example, in the control of hyperproliferative disorders. The growth of cells such as adipocytes can be regulated with agents identified using ztg2 as a marker, providing a means for controlling fat depots in certain forms of obesity without the necessity of surgical intervention.

Ztg2 antagonists include inhibitory polynucleotides, which can be used to inhibit ztg2 gene transcription or translation in a patient or test animal. Polynucleotides that are complementary to a segment of a ztg2-encoding polynucleotide (e.g., a polynucleotide as set forth in SEQ ID NO: 1) are designed to bind to ztg2-encoding mRNA and to inhibit translation of such mRNA. Such antisense polynucleotides can be targetted to specific tissues using a gene therapy approach with specific vectors and/or promoters, such as viral delivery systems. Ribozymes can also be used as ztg2 antagonists. Ribozymes are RNA molecules that contains a catalytic center and a target RNA binding portion. The term includes RNA enzymes, self-splicing RNAs, self-cleaving RNAs, and nucleic acid molecules that perform these catalytic functions. A ribozyme selectively binds to a target RNA molecule through complementary base pairing, bringing the catalytic center into close proximity with the target sequence. The ribozyme then cleaves the target RNA and is released, after which it is able to bind and cleave additional molecules. A nucleic acid molecule that encodes a ribozyme is termed a "ribozyme gene." Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). An expression vector can be constructed in which a regulatory element is operably linked to a nucleotide sequence that encodes a ribozyme. In another approach, expression vectors can be constructed in which a regulatory element directs the production of RNA transcripts capable of promoting Rnase P-mediated cleavage of mRNA molecules that encode a ztg2 polypeptide. According to this approach, an external guide sequence can be constructed for directing the endogenous ribozyme, Rnase P, to a particular species of intracellular mRNA, which is subsequently cleaved by the cellular ribozyme (see, for example, Altman et al., U.S. Pat. No. 5,168,053; Yuan et al., *Science* 263:1269, 1994; Pace et al., WIPO Publication No. WO 96/18733; George et al., WIPO Publication No. WO 96/21731; and Werner et al., WIPO Publication No. WO 97/33991). An external guide sequence generally comprises a ten- to fifteen-nucleotide sequence complementary to ztg2 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by Rnase P at the nucleotide located at the 5'-side of the base-paired region.

Polynucleotides that encode ztg2 can be directly detected in cells using labeled synthetic oligonucleotide probes in a hybridization procedure similar to the Southern or dot blot. Polymerase chain reaction can be used to amplify DNA sequences, which are subsequently detected by their characteristic size on agarose gels, Southern blots of the gels using ztg2 sequences as probes, or dot blots using similar probes. Such probes will comprise from about 14 nucleotides to about 25 or more nucleotides, sometimes 40–60 nucleotides, and in some instances a substantial portion or even an entire ztg2 cDNA, gene, or coding region thereof. Probes are ordinarily labeled to provide a detectable signal. Suitable labels include enzymes, biotin, radionuclides, fluorophores, chemiluminescers, paramagnetic particles, and the like.

The present invention also provides reagents for use in diagnostic applications. For example, the ztg2 gene, a probe comprising ztg2 DNA or RNA, or a subsequence thereof can be used to determine the presence of mutations at or near the ztg2 locus at human chromosome 15q15.3. This region of human chromosome 15 has been linked to Fanconi renotubular sydrome (Lichter-Konecki et al., *Am. J. Hum. Genet.* 68:264–268, 2001). Detectable chromosomal aberrations at the ztg2 gene locus include, but are not limited to, aneuploidy, gene copy number changes, insertions, deletions, restriction site changes, translocations, and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targetted for analysis. For gross analysis of genes, a polynucleotide probe may comprise an entire exon or more.

Probes will generally comprise a polynucleotide linked to a signal-generating moiety such as a radionucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (c) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; A. J. Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA–RNA hybrid) is exposed to Rnase. Hybridized regions of the RNA are protected from digestion. Within PCR assays, a patient genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–38, 1991).

Polynucleotides and polypeptides of the present invention will additionally find use as educational tools within laboratory practicum kits for courses related to genetics, molecular biology, protein chemistry, and antibody production and analysis. Due to their unique polynucleotide and polypeptide sequences, ztg2 polynucleotides and polypeptides can be used as standards or as "unknowns" for testing purposes. For example, ztg2 polynucleotides can be used as aids in teaching a student how to prepare expression constructs for bacterial, viral, and/or mammalian expression, including fusion constructs, wherein a ztg2 polynucleotide is to be expressed; for determining the restriction endonuclease cleavage sites of the polynucleotides; determining mRNA and DNA localization of ztg2 polynucleotides in tissues (i.e., by Northern and Southern blotting as well as polymerase chain reaction); and for identifying related polynucleotides and polypeptides by nucleic acid hybridization. Ztg2 polypeptides can be used educationally as aids in teaching preparation of antibodies; identification of proteins by Western blotting; protein purification; determination of the weight of expressed ztg2 polypeptides as a ratio to total protein expressed; identification of peptide cleavage sites; coupling amino and carboxyl terminal tags; amino acid sequence analysis; as well as, but not limited to, monitoring biological activities of both the native and tagged protein in vitro and in vivo. Ztg2 polypeptides can also be used to teach analytical skills such as mass spectrometry, circular dichroism, x-ray crystallography, and nuclear magnetic resonance spectroscopy. For example, a kit containing a ztg2 polypeptide can be given to a student to analyze. Since the amino acid sequence would be known by the instructor, the protein can be given to the student as a test to determine the skills or develop the skills of the student, and the instructor would then know whether or not the student had correctly analyzed the polypeptide. Since every polypeptide is unique, the educational utility of ztg2 would be unique unto itself.

The invention is further illustrated by the following, non-limiting examples.

EXAMPLE 1

Recombinant human ztg2 is produced in *E. coli* using a $His_6$ tag/maltose binding protein (MBP) double affinity fusion system as generally disclosed by Pryor and Leiting, *Prot. Expr. Pur.* 10:309–319, 1997. A thrombin cleavage site is placed at the junction between the affinity tag and ztg2 sequences.

The fusion construct is assembled in the vector pTAP98, which comprises sequences for replication and selection in *E. coli* and yeast, the *E. coli* tac promoter, and a unique SmaI site just downstream of the MBP-$His_6$-thrombin site coding sequences. The ztg2 cDNA (SEQ ID NO:1) is amplified by PCR using primers each comprising 40 bp of sequence homologous to vector sequence and 25 bp of sequence that anneals to the cDNA. The reaction is run using Pwo DNA polymerase (Boehringer Mannheim, Indianapolis, Ind.) for 30 cycles of 94° C., 30 seconds; 60° C., 60 seconds; and 72° C., 60 seconds. One microgram of the resulting fragment is mixed with 100 ng of SmaI-cut pTAP98, and the mixture was transformed into yeast (*Saccharomyces cerevisiae*) to assemble the vector by homologous recombination (Oldenburg et al., *Nucl. Acids. Res.* 25:451–452, 1997). Ura$^+$transformants are selected.

Plasmid DNA is prepared from yeast transformants and transformed into *E. coli* MC1061. Pooled plasmid DNA is then prepared from the MC1061 transformants by the miniprep method after scraping an entire plate. Plasmid DNA is analyzed by restriction digestion.

*E. coli* strain BL21 is used for expression of ztg2. Cells are transformed by electroporation and grown on minimal glucose plates containing casamino acids and ampicillin.

Protein expression is analyzed by gel electrophoresis. Cells are grown in liquid medium containing ampicillin. After one hour at 37° C., IPTG is added to a final concentration of 1 mM, and the cells are grown for an additional 2–3 hours at 37° C. Cells are disrupted using glass beads, and extracts are prepared.

EXAMPLE 2

A truncated ztg2 polypeptide is produced in *E. coli*. A fragment of the ztg2 cDNA (SEQ ID NO: 1) encoding residues 1–462 of SEQ ID NO:2 is amplified by PCR essentially as disclosed in Example 1. An expression vector is assembled by homologous recombination in *S. cerevisiae*, and the DNA is recovered and transformed into *E. coli* strain MC1061. Pooled plasmid DNA is then prepared from the MC1061 transformants by the miniprep method after scraping an entire plate. Plasmid DNA is analyzed by restriction digestion.

*E. coli* strain BL21 is used for expression of ztg2. Cells are transformed by electroporation and grown on minimal glucose plates containing casamino acids and ampicillin. After one hour at 37° C., IPTG is added to a final concentration of 1 mM, and the cells are grown for an additional 2–3 hours at 37° C. Cells are disrupted using glass beads, and extracts are prepared.

EXAMPLE 3

A mammalian cell expression vector encoding ztg2 is constructed via homologous recombination. Ztg2 cDNA is isolated by PCR using primers that comprise, from 5' to 3' end, 40 bp of flanking sequence from the vector and 17 bp corresponding to the amino and carboxyl termini from the open reading frame of ztg2. The resulting PCR product includes flanking regions at the 5' and 3' ends corresponding to the vector sequences flanking the ztg2 insertion point. Ten µl of the 100 µl PCR reaction mixture is run on a 0.8% low-melting-temperature agarose (SeaPlaque GTG®; FMC BioProducts, Rockland, Me.) gel with 1×TBE buffer for analysis. The remaining 90 µl of the reaction mixture is precipitated with the addition of 5 µl M NaCl and 250 µl of absolute ethanol.

The plasmid pZMP6, which has been cut with SmaI, is used for recombination with the PCR fragment. Plamid pZMP6 is a mammalian expression vector containing an expression cassette having the cytomegalovirus immediate early promoter, multiple restriction sites for insertion of coding sequences, a stop codon, and a human growth hormone terminator; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It was constructed from pZP-9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain.

One hundred microliters of competent yeast (*S. cerevisiae*) cells are combined with 10 µl of the DNA preparations from above and transferred to a 0.2-cm electroporation cuvette. The yeast/DNA mixture is electropulsed using power supply (BioRad Laboratories, Hercules, Calif.) settings of 0.75 kV (5 kV/cm), ∞ohms, 25 µF. To each cuvette is added 600 µof 1.2 M sorbitol, and the yeast is plated in two 300-µl aliquots onto two URA-D plates and incubated at 30° C. After about 48 hours, the Ura$^+$yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid-washed glass beads and 200 µl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 µl ethanol (EtOH), followed by centrifugation for 10 minutes at 4° C. The DNA pellet is resuspended in 10 µl $H_2O$.

Transformation of electrocompetent *E. coli* host cells (Electromax DH10B™ cells; obtained from Life Technologies, Inc., Gaithersburg, Md.) is done with 0.5–2 ml yeast DNA prep and 40 µl of cells. The cells are electropulsed at 1.7 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is plated in 250-µl aliquots on four LB AMP plates (LB broth (Lennox), 1.8% Bacto™ Agar (Difco), 100 mg/L Ampicillin).

Individual clones harboring the correct expression construct for ztg2 are identified by restriction digest to verify the presence of the ztg2 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated pZMP6/ztg2.

EXAMPLE 4

Full-length ztg2 protein is produced in BHK cells transfected with pZMP6/ztg2 (Example 3). BHK 570 cells (ATCC CRL-10314) are plated in 10-cm tissue culture dishes and allowed to grow to approximately 50 to 70% confluence overnight at 37° C., 5% $CO_2$, in DMEM/FBS media (DMEM, Gibco/BRL High Glucose; Life Technologies), 5% fetal bovine serum (Hyclone, Logan, Utah), 1 mM L-glutamine (JRH Biosciences, Lenexa, Kans.), 1 mM sodium pyruvate (Life Technologies). The cells are then transfected with pZMP6/ztg2 by liposome-mediated transfection (using Lipofectamine™; Life Technologies), in serum free (SF) media (DMEM supplemented with 10 mg/ml transferrin, 5 mg/ml insulin, 2 mg/ml fetuin, 1% L-glutamine and 1% sodium pyruvate). The plasmid is diluted into 15-ml tubes to a total final volume of 640 µl with SF media. 35 µl of the lipid mixture is mixed with 605 µl of SF medium, and the resulting mixture is allowed to incubate approximately 30 minutes at room temperature. Five milliliters of SF media is then added to the DNA:lipid mixture. The cells are rinsed once with 5 ml of SF media, aspirated, and the DNA:lipid mixture is added. The cells are incubated at 37° C. for five hours, then 6.4 ml of DMEM/10% FBS, 1% PSN media is added to each plate. The plates are incubated at 37° C. overnight, and the DNA:lipid mixture is replaced with fresh 5% FBS/DMEM media the next day. On day 5 post-transfection, the cells are split into T-162 flasks in selection medium (DMEM+5% FBS, 1% L-Gln, 1% NaPyr, 1 µM methotrexate). Approximately 10 days post-transfection, two 150-mm culture dishes of methotrexate-resistant colonies from each transfection are trypsinized, and the cells are pooled and plated into a T-162 flask and transferred to large-scale culture.

EXAMPLE 5

To construct a yeast expression vector, ztg2 cDNA (SEQ ID NO: 1) is cloned into the yeast vector pDPOT (deposited with American Type Culture Collection as an *E. coli* HB101 transformant under Accession No. 68001) essentially as disclosed in European Pat. No. 0 284 044. The resulting expression vector comprises an expression unit comprising the *S. cerevisiae* ADH2-4$^c$ promoter, ztg2 sequence, and TPI1 terminator, and the *Schizosaccharomyces pombe* POT1 gene selectable marker. The expression vector is transformed into *S. cerevisiae* strain ZM118 (a MATa/MATα diploid homozygous for leu2-3, 112 ura3 tpil::URA3$^+$bar1 pep4::URA$^+$[cir$^o$]).

Transformants are cultured and protein is recovered essentially as disclosed in U.S. Pat. No. 5,612,456. The transformed cells are inoculated at approximately 0.1 g/l into twenty liters of a pH5.5 culture medium containing 25 g/l yeast extract, 22.5 g/l $(NH_4)_2SO_4$, 6.5 g/l $KH_2PO_4$, 3 g/l $MgSO_4$, and 0.5% glucose. The cells are provided with a glucose feed from 0 to 24 hours and an ethanol feed from 0 to 12 hours. The cells are grown at 30° C. to a final density of approximately 60 g/l. To recover ztg2 polypeptide, the cells are harvested by concentration using a 0.2µ hollow fiber cartridge, then diluted to 40% wet weight in lysis buffer (50 mM Tris-HCl, pH 7.4, 150 mM NaCl, 15 mM EDTA, 5 mM 2-mercaptoethanol, 1 mM PMSF) and lysed by physical disruption with glass beads. The lysate is clarified by centrifugation, and the ztg2-containing supernatant is recovered.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. An isolated polypeptide wherein the polypeptide consists of residues 1 through 704 of SEQ ID NO:2 or residues 1–462 of SEQ ID NO:2.

2. A polypeptide produced by a method comprising:

culturing a cell containing an expression vector comprising the following operably linked elements:

(a) a transcription promoter;

(b) a DNA segment encoding a polypeptide consisting of residues 1 through 704 of SEQ ID NO:2 or residues 1–462 of SEQ ID NO:2; and (c) a transcription terminator under conditions whereby the DNA segment is expressed; and recovering the polypeptide encoded by the DNA segment.

* * * * *

SEQUENCE LISTING

<160> NUMBER OF SEQ ID NOS: 7

<210> SEQ ID NO 1
<211> LENGTH: 2290
<212> TYPE: DNA
<213> ORGANISM: Homo sapiens
<220> FEATURE:
<221> NAME/KEY: CDS
<222> LOCATION: (1)...(2115)

<400> SEQUENCE: 1

```
ttg cgg ctt gag tct gtc gac ctg cag agc tcc agg aac aac aag gag      48
Leu Arg Leu Glu Ser Val Asp Leu Gln Ser Ser Arg Asn Asn Lys Glu
 1               5                  10                  15 cac cac acg cag gag atg ggc gtc aag cgg ctc act gtg cgc cgc ggc      96
His His Thr Gln Glu Met Gly Val Lys Arg Leu Thr Val Arg Arg Gly
             20                  25                  30 cag ccc ttc tac ctc cgg ctg agc ttc agc cga ccc ttc cag tcc cag     144
Gln Pro Phe Tyr Leu Arg Leu Ser Phe Ser Arg Pro Phe Gln Ser Gln
```

```
                 35                  40                  45
aac gac cac atc acc ttt gtg gct gag acc gga ccc aag ccg tca gag    192
Asn Asp His Ile Thr Phe Val Ala Glu Thr Gly Pro Lys Pro Ser Glu
         50                  55                  60 ctg ctg ggg acc cga gcc aca ttc ttc ctc acc cgg gtc cag ccc ggg    240
Leu Leu Gly Thr Arg Ala Thr Phe Phe Leu Thr Arg Val Gln Pro Gly
 65                  70                  75                  80 aat gtc tgg agc gct tct gat ttc acc att gac tcc aac tct ctc caa    288
Asn Val Trp Ser Ala Ser Asp Phe Thr Ile Asp Ser Asn Ser Leu Gln
                         85                  90                  95 gtt tcc ctt ttc aca cca gcc aat gca gtt att ggc cat tac act ctg    336
Val Ser Leu Phe Thr Pro Ala Asn Ala Val Ile Gly His Tyr Thr Leu
                100                 105                 110 aaa ata gag atc tct cag ggc caa ggt cac agt gtg act tac ccg ctg    384
Lys Ile Glu Ile Ser Gln Gly Gln Gly His Ser Val Thr Tyr Pro Leu
            115                 120                 125 gga act ttc atc cta ctt ttt aac cct tgg agt cca gag gac gac gtc    432
Gly Thr Phe Ile Leu Leu Phe Asn Pro Trp Ser Pro Glu Asp Asp Val
130                 135                 140 tac ctg cca agt gaa ata ctg ctg cag gag tat atc atg cga gat tat    480
Tyr Leu Pro Ser Glu Ile Leu Leu Gln Glu Tyr Ile Met Arg Asp Tyr
145                 150                 155                 160 ggc ttt gtt tac aag ggt cat gaa aga ttc atc acc tcc tgg ccc tgg    528
Gly Phe Val Tyr Lys Gly His Glu Arg Phe Ile Thr Ser Trp Pro Trp
                165                 170                 175 aac tac ggg cag ttt gaa gag gac ata ata gac atc tgc ttt gag atc    576
Asn Tyr Gly Gln Phe Glu Glu Asp Ile Ile Asp Ile Cys Phe Glu Ile
                180                 185                 190 ctg aac aag agc ctg tat cac tta aag aac ccg gcc aaa gac tgt tcc    624
Leu Asn Lys Ser Leu Tyr His Leu Lys Asn Pro Ala Lys Asp Cys Ser
            195                 200                 205 cag cgg aac gac gtg gtg tat gtg tgc agg gtg gtg agt gcc atg atc    672
Gln Arg Asn Asp Val Val Tyr Val Cys Arg Val Val Ser Ala Met Ile
        210                 215                 220 aac agc aac gat gac aat ggc gtg ctg cag ggg aac tgg ggc gag gac    720
Asn Ser Asn Asp Asp Asn Gly Val Leu Gln Gly Asn Trp Gly Glu Asp
225                 230                 235                 240 tac tcc aaa ggg gtc agt cct ctg gag tgg aag ggc agc gtg gcc atc    768
Tyr Ser Lys Gly Val Ser Pro Leu Glu Trp Lys Gly Ser Val Ala Ile
                245                 250                 255 cta cag cag tgg tca gcc agg ggc ggg cag cct gtg aag tac gga cag    816
Leu Gln Gln Trp Ser Ala Arg Gly Gly Gln Pro Val Lys Tyr Gly Gln
                260                 265                 270 tgc tgg gtc ttc gcc tct gtt atg tgc acc gta atg aga tgc tta ggt    864
Cys Trp Val Phe Ala Ser Val Met Cys Thr Val Met Arg Cys Leu Gly
            275                 280                 285 gtt cca acc cgt gtt gtt tcc aat ttc cgt tcc gcg cac aac gtg gat    912
Val Pro Thr Arg Val Val Ser Asn Phe Arg Ser Ala His Asn Val Asp
        290                 295                 300 agg aac ttg acc atc gat acg tac tat gac cga aat gcc gag atg ctg    960
Arg Asn Leu Thr Ile Asp Thr Tyr Tyr Asp Arg Asn Ala Glu Met Leu
305                 310                 315                 320 tca act cag aaa cga gac aaa ata tgg aac ttc cac gtc tgg aat gag   1008
Ser Thr Gln Lys Arg Asp Lys Ile Trp Asn Phe His Val Trp Asn Glu
                325                 330                 335 tgc tgg atg atc cgg aaa gat ctc cca cca gga tac aac ggg tgg cag   1056
Cys Trp Met Ile Arg Lys Asp Leu Pro Pro Gly Tyr Asn Gly Trp Gln
                340                 345                 350 gtt ctg gac ccc act ccc cag cag acc agc agt ggg ctg ttc tgc tgt   1104
```

|   |   |
|---|---|
| Val Leu Asp Pro Thr Pro Gln Gln Thr Ser Ser Gly Leu Phe Cys Cys<br>355                          360                    365 |   |
| ggc cct gcc tct gtg aag gcc atc agg gaa ggg gat gtc cac ctg gcc<br>Gly Pro Ala Ser Val Lys Ala Ile Arg Glu Gly Asp Val His Leu Ala<br>370                       375                     380 | 1152 |
| tat gac acc cct ttt gtg tat gcc gag gtg aac gcc gat gaa gtc att<br>Tyr Asp Thr Pro Phe Val Tyr Ala Glu Val Asn Ala Asp Glu Val Ile<br>385                          390                    395                   400 | 1200 |
| tgg ctc ctt ggg gat ggc cag gcc cag gaa atc ctg gcc cac aac acc<br>Trp Leu Leu Gly Asp Gly Gln Ala Gln Glu Ile Leu Ala His Asn Thr<br>                     405                    410                   415 | 1248 |
| agt tcc atc ggg aag gag atc agc act aag atg gtg gga tca gac cag<br>Ser Ser Ile Gly Lys Glu Ile Ser Thr Lys Met Val Gly Ser Asp Gln<br>                  420                    425                   430 | 1296 |
| cgc cag agc atc acc agc tcc tac aag tac cca gaa gga tcc cct gag<br>Arg Gln Ser Ile Thr Ser Ser Tyr Lys Tyr Pro Glu Gly Ser Pro Glu<br>435                          440                    445 | 1344 |
| gag aga gct gtc ttc atg aag gct tct cgg aaa atg ctg ggc ccc caa<br>Glu Arg Ala Val Phe Met Lys Ala Ser Arg Lys Met Leu Gly Pro Gln<br>450                       455                    460 | 1392 |
| aga gct tct ttg ccc ttc ctg gat ctc ctg gag tct ggg ggt ctt agg<br>Arg Ala Ser Leu Pro Phe Leu Asp Leu Leu Glu Ser Gly Gly Leu Arg<br>465                          470                    475                   480 | 1440 |
| gat cag cca gcg cag ctg cag ctt cac ctg gcc agg ata ccc gag tgg<br>Asp Gln Pro Ala Gln Leu Gln Leu His Leu Ala Arg Ile Pro Glu Trp<br>                     485                    490                   495 | 1488 |
| ggc cag gac ctg cag ctg ctg ctg cgt atc cag agg gtg cca gac agc<br>Gly Gln Asp Leu Gln Leu Leu Leu Arg Ile Gln Arg Val Pro Asp Ser<br>                  500                    505                   510 | 1536 |
| acc cac cct cgg ggg ccc atc gga ctg gtg gtg cgc ttc tgt gca cag<br>Thr His Pro Arg Gly Pro Ile Gly Leu Val Val Arg Phe Cys Ala Gln<br>                515                    520                   525 | 1584 |
| gcc ctg ctg cat ggg ggt ggt acc cag aag ccc ttc tgg agg cac aca<br>Ala Leu Leu His Gly Gly Gly Thr Gln Lys Pro Phe Trp Arg His Thr<br>530                          535                    540 | 1632 |
| gtg cgg atg aac ctg gac ttt ggg aag gag aca cag tgg ccg ctc ctc<br>Val Arg Met Asn Leu Asp Phe Gly Lys Glu Thr Gln Trp Pro Leu Leu<br>545                          550                    555                   560 | 1680 |
| ctg ccc tac agc aat tac aga aac aag cta acg gac gaa aag ctc atc<br>Leu Pro Tyr Ser Asn Tyr Arg Asn Lys Leu Thr Asp Glu Lys Leu Ile<br>                     565                    570                   575 | 1728 |
| cgc gtg tct ggc atc gcc gag gtt gaa gag aca ggg agg tcc atg ctg<br>Arg Val Ser Gly Ile Ala Glu Val Glu Glu Thr Gly Arg Ser Met Leu<br>                  580                    585                   590 | 1776 |
| gtc cta aaa gat atc tgt ctg gag cct ccc cac ttg tct att gag gtg<br>Val Leu Lys Asp Ile Cys Leu Glu Pro Pro His Leu Ser Ile Glu Val<br>                595                    600                   605 | 1824 |
| tct gag agg gct gag gtg ggc aag gcg ctg aga gtc cat gtc acc ctc<br>Ser Glu Arg Ala Glu Val Gly Lys Ala Leu Arg Val His Val Thr Leu<br>610                          615                    620 | 1872 |
| acc aac acc tta atg gtg gct ctg agc agc tgc acg atg gtg ctg gaa<br>Thr Asn Thr Leu Met Val Ala Leu Ser Ser Cys Thr Met Val Leu Glu<br>625                          630                    635                   640 | 1920 |
| gga agc ggc ctc atc aat ggg cag ata gca aag gac ctt gga act ctg<br>Gly Ser Gly Leu Ile Asn Gly Gln Ile Ala Lys Asp Leu Gly Thr Leu<br>                     645                    650                   655 | 1968 |
| gtg gcc gga cac acc ctc caa att caa ctg gac ctc tac ccg acc aaa<br>Val Ala Gly His Thr Leu Gln Ile Gln Leu Asp Leu Tyr Pro Thr Lys<br>660                          665                    670 | 2016 |

-continued

| | | | | | | | | | | | | | | |
|---|---|---|---|---|---|---|---|---|---|---|---|---|---|---|
| gct | gga | ccc | cgc | cag | ctc | cag | gtt | ctc | atc | agc | agc | aac | gag | gtc aag |
| Ala | Gly | Pro | Arg | Gln | Leu | Gln | Val | Leu | Ile | Ser | Ser | Asn | Glu | Val Lys |
| | | 675 | | | | 680 | | | | 685 | | | | |

2064

| | | | | | | | | | | | | | | |
|---|---|---|---|---|---|---|---|---|---|---|---|---|---|---|
| gag | atc | aaa | ggc | tac | aag | gac | atc | ttc | gtc | act | gtg | gct | ggg | gct ccc |
| Glu | Ile | Lys | Gly | Tyr | Lys | Asp | Ile | Phe | Val | Thr | Val | Ala | Gly | Ala Pro |
| 690 | | | | | 695 | | | | | 700 | | | | |

2112 tga gacccgccct ccagctgccc tccctggcac ccctgcccca cctggctcct    2165
* ttctactcct ggctatgtcg tcttggctcc acctctgtcc tctctctagc ctgcctggga    2225
atgaatgaag ctctgttaga aacaccgtgt gctttgggaa gagacaataa agatgtcttt    2285
attta    2290

<210> SEQ ID NO 2
<211> LENGTH: 704
<212> TYPE: PRT
<213> ORGANISM: Homo sapiens

<400> SEQUENCE: 2

Leu Arg Leu Glu Ser Val Asp Leu Gln Ser Ser Arg Asn Asn Lys Glu
  1               5                  10                  15

His His Thr Gln Glu Met Gly Val Lys Arg Leu Thr Val Arg Arg Gly
             20                  25                  30

Gln Pro Phe Tyr Leu Arg Leu Ser Phe Ser Arg Pro Phe Gln Ser Gln
         35                  40                  45

Asn Asp His Ile Thr Phe Val Ala Glu Thr Gly Pro Lys Pro Ser Glu
     50                  55                  60

Leu Leu Gly Thr Arg Ala Thr Phe Phe Leu Thr Arg Val Gln Pro Gly
 65                  70                  75                  80

Asn Val Trp Ser Ala Ser Asp Phe Thr Ile Asp Ser Asn Ser Leu Gln
                 85                  90                  95

Val Ser Leu Phe Thr Pro Ala Asn Ala Val Ile Gly His Tyr Thr Leu
            100                 105                 110

Lys Ile Glu Ile Ser Gln Gly Gln Gly His Ser Val Thr Tyr Pro Leu
        115                 120                 125

Gly Thr Phe Ile Leu Leu Phe Asn Pro Trp Ser Pro Glu Asp Asp Val
    130                 135                 140

Tyr Leu Pro Ser Glu Ile Leu Leu Gln Glu Tyr Ile Met Arg Asp Tyr
145                 150                 155                 160

Gly Phe Val Tyr Lys Gly His Glu Arg Phe Ile Thr Ser Trp Pro Trp
                165                 170                 175

Asn Tyr Gly Gln Phe Glu Glu Asp Ile Ile Asp Ile Cys Phe Glu Ile
            180                 185                 190

Leu Asn Lys Ser Leu Tyr His Leu Lys Asn Pro Ala Lys Asp Cys Ser
        195                 200                 205

Gln Arg Asn Asp Val Val Tyr Val Cys Arg Val Ser Ala Met Ile
    210                 215                 220

Asn Ser Asn Asp Asp Asn Gly Val Leu Gln Gly Asn Trp Gly Glu Asp
225                 230                 235                 240

Tyr Ser Lys Gly Val Ser Pro Leu Glu Trp Lys Gly Ser Val Ala Ile
                245                 250                 255

Leu Gln Gln Trp Ser Ala Arg Gly Gly Gln Pro Val Lys Tyr Gly Gln
            260                 265                 270

Cys Trp Val Phe Ala Ser Val Met Cys Thr Val Met Arg Cys Leu Gly
        275                 280                 285

```
Val Pro Thr Arg Val Val Ser Asn Phe Arg Ser Ala His Asn Val Asp
    290                 295                 300

Arg Asn Leu Thr Ile Asp Thr Tyr Tyr Asp Arg Asn Ala Glu Met Leu
305                 310                 315                 320

Ser Thr Gln Lys Arg Asp Lys Ile Trp Asn Phe His Val Trp Asn Glu
                325                 330                 335

Cys Trp Met Ile Arg Lys Asp Leu Pro Pro Gly Tyr Asn Gly Trp Gln
            340                 345                 350

Val Leu Asp Pro Thr Pro Gln Gln Thr Ser Ser Gly Leu Phe Cys Cys
        355                 360                 365

Gly Pro Ala Ser Val Lys Ala Ile Arg Glu Gly Asp Val His Leu Ala
    370                 375                 380

Tyr Asp Thr Pro Phe Val Tyr Ala Glu Val Asn Ala Asp Glu Val Ile
385                 390                 395                 400

Trp Leu Leu Gly Asp Gly Gln Ala Gln Glu Ile Leu Ala His Asn Thr
                405                 410                 415

Ser Ser Ile Gly Lys Glu Ile Ser Thr Lys Met Val Gly Ser Asp Gln
                420                 425                 430

Arg Gln Ser Ile Thr Ser Ser Tyr Lys Tyr Pro Glu Gly Ser Pro Glu
        435                 440                 445

Glu Arg Ala Val Phe Met Lys Ala Ser Arg Lys Met Leu Gly Pro Gln
450                 455                 460

Arg Ala Ser Leu Pro Phe Leu Asp Leu Leu Glu Ser Gly Gly Leu Arg
465                 470                 475                 480

Asp Gln Pro Ala Gln Leu Gln Leu His Leu Ala Arg Ile Pro Glu Trp
                485                 490                 495

Gly Gln Asp Leu Gln Leu Leu Arg Ile Gln Arg Val Pro Asp Ser
                500                 505                 510

Thr His Pro Arg Gly Pro Ile Gly Leu Val Val Arg Phe Cys Ala Gln
        515                 520                 525

Ala Leu Leu His Gly Gly Thr Gln Lys Pro Phe Trp Arg His Thr
530                 535                 540

Val Arg Met Asn Leu Asp Phe Gly Lys Glu Thr Gln Trp Pro Leu Leu
545                 550                 555                 560

Leu Pro Tyr Ser Asn Tyr Arg Asn Lys Leu Thr Asp Glu Lys Leu Ile
                565                 570                 575

Arg Val Ser Gly Ile Ala Glu Val Glu Glu Thr Gly Arg Ser Met Leu
                580                 585                 590

Val Leu Lys Asp Ile Cys Leu Glu Pro Pro His Leu Ser Ile Glu Val
        595                 600                 605

Ser Glu Arg Ala Glu Val Gly Lys Ala Leu Arg Val His Val Thr Leu
610                 615                 620

Thr Asn Thr Leu Met Val Ala Leu Ser Ser Cys Thr Met Val Leu Glu
625                 630                 635                 640

Gly Ser Gly Leu Ile Asn Gly Gln Ile Ala Lys Asp Leu Gly Thr Leu
                645                 650                 655

Val Ala Gly His Thr Leu Gln Ile Gln Leu Asp Leu Tyr Pro Thr Lys
                660                 665                 670

Ala Gly Pro Arg Gln Leu Gln Val Leu Ile Ser Ser Asn Glu Val Lys
            675                 680                 685

Glu Ile Lys Gly Tyr Lys Asp Ile Phe Val Thr Val Ala Gly Ala Pro
690                 695                 700
```

```
<210> SEQ ID NO 3
<211> LENGTH: 19000
<212> TYPE: DNA
<213> ORGANISM: Homo sapiens
<220> FEATURE:
<221> NAME/KEY: exon
<222> LOCATION: (180)...(354)
<221> NAME/KEY: exon
<222> LOCATION: (849)...(1094)
<221> NAME/KEY: exon
<222> LOCATION: (1706)...(1824)
<221> NAME/KEY: exon
<222> LOCATION: (6134)...(6262)
<221> NAME/KEY: exon
<222> LOCATION: (6346)...(6523)
<221> NAME/KEY: exon
<222> LOCATION: (8853)...(8991)
<221> NAME/KEY: exon
<222> LOCATION: (11186)...(11289)
<221> NAME/KEY: exon
<222> LOCATION: (11720)...(11962)
<221> NAME/KEY: exon
<222> LOCATION: (13855)...(14181)
<221> NAME/KEY: exon
<222> LOCATION: (14529)...(14689)
<221> NAME/KEY: exon
<222> LOCATION: (16811)...(16944)
<221> NAME/KEY: exon
<222> LOCATION: (17192)...(17522)

<400> SEQUENCE: 3
```

| | | | | |
|---|---|---|---|---|
| ggaagcacca | cgcctcgcgc | tgggacagaa | tttcggcgtc aagaaaatgc | cctcggcgga | 60 |
| atgcacgccc | caccacccgc | cgcacttccc | agaaatgact gagaagccac | aagggatgcc | 120 |
| tgagcccagg | ggactgcagg | tgggcgtgac | ctgtcccctc ctctccccta | gtggcaacct | 180 |
| tgcggcttga | gtctgtcgac | ctgcagagct | ccaggaacaa caaggagcac | acacgcagg | 240 |
| agatgggcgt | caagcggctc | actgtgcgcc | gcggccagcc cttctacctc | cggctgagct | 300 |
| tcagccgacc | cttccagtcc | cagaacgacc | acatcacctt tgtggctgag | accggtgagt | 360 |
| ttgccctgtc | ccaaggcccc | gcaggttccg | tcaaaatgag ggcatttaca | gagtctgcct | 420 |
| gcggggcccc | tgccttcccc | acctgagctg | ccctccactt tcttgtcctg | ggagccccag | 480 |
| gcccctcatg | ctcaggaccc | tgttagtgct | gttaaggaga gatttggtca | actcggcaaa | 540 |
| ctgaggttgt | ggcagttaac | aaccgacctg | tagatacaca acaagcactg | tgctaaaact | 600 |
| ttacacacat | tagctcattt | aatccccagg | acaagacttt caggtggtac | tattatgatc | 660 |
| ccctttttaac | agattaaaaa | acggaggcct | ggggggtctta aatggtttgc | ctgaggacac | 720 |
| tcggtggcag | taaaagccaa | aagcattagc | aggtggtggg agaaggtgac | ggtccttccg | 780 |
| actcccctgg | aatcatatac | catacaggtt | ttttgagcct cactgtgggg | tcattctctc | 840 |
| ctacacagga | cccaagccgt | cagagctgct | ggggacccga gccacattct | tcctcacccg | 900 |
| ggtccagccc | gggaatgtct | ggagcgcttc | tgatttcacc attgactcca | actctctcca | 960 |
| agtttcccctt | ttcacaccag | ccaatgcagt | tattggccat tacactctga | aaatagagat | 1020 |
| ctctcagggc | caaggtcaca | gtgtgactta | cccgctggga actttcatcc | tacttttttaa | 1080 |
| cccttggagt | ccaggtagga | tgtgcccaca | gcttgtattg ctaacctgat | ccattgggaa | 1140 |
| ggccctgtga | ggttctttgg | aaaaagccca | gaaaataaat cgccacatag | ctatgcaatg | 1200 |
| tagtagcgtg | tgctctcaca | aaaatcatct | ttacaaagaa tttctaatgg | catgaggaaa | 1260 |
| gtattcatga | cgtgatgtta | agtgaaaaca | ttgaaacatt tcctaatatg | agcctaattg | 1320 |
| tattaagtat | gcacagaaag | agagagtggc | tagaatacac caaaacataa | cggtgggtgt | 1380 |
| ctctgagtag | tgggagtgag | cagtttccat | tgtcttctac ccatctatct | gtattttctg | 1440 |

-continued

```
aatctctaca ataagccaac tctacaatca gtcactttta caatcaagaa aagatcgttg    1500
gtttttaaag tgtacattgt atttctggct tctagaaaag cacatagtag acctttaagg    1560
gggtctagtc ttaatttctg ttgctatcaa cccatcgact gttcctcctg ttttccagaa    1620
acacgttgtc gttactgttt tttaatttaa tactctgttt ttttggtttg gggttttgcc    1680
ccctccacta ctcttaactg ctcagaggac gacgtctacc tgccaagtga atactgctg     1740
caggagtata tcatgcgaga ttatggcttt gtttacaagg gtcatgaaag attcatcacc    1800
tcctggccct ggaactacgg gcaggtaaca ctattaccca atgtgggcct ggggtgggct    1860
ccctaaggct ggtccttaca caaccctgtt atgtaaggct gttatattac acagccctca    1920
tagagggcca ctaatacagg cgagggtgtg aggggcttgg ccagcttcac atccagtgag    1980
aggggcaagg aaggaagggg tggatgtctt tccttttag ttttaacat tttattatga      2040
aaaaccttaa aacataatca agtagacag gctactacaa tagatctccc tgtacccacc    2100
tctcagcttc agtagtgatc aatgtatcat gagtctgttt catcaacacc ggggtttgc     2160
aaactacagc ccacagacca aatgtggcct actgcctgtt tagcccatga gctgagaata    2220
gttttcacgt tttttacttg ttgaaaagga attgtaaaag aataatattt tgtgatgtga    2280
aaattatatg aaattcaaat ttcagcgtgc acaaatagca ttttattgca aatagccatg    2340
ttcattcatt tagatgtagt ctgtggctgc ttgcatgctg cattggcaga attgagttat    2400
taagacagag acctgcttca acacatgcaa atcaataaac gtaatccagc atataaacag    2460
aaccaacgac aaaaactgca tgattatctc aatagatgca gaaaaggcct ttgacaaaat    2520
tcaacaacct tcatgctaaa aactctcaat aaattaggta ttgatgggac atatctcaaa    2580
ataataagag ctacctatga caaacccaca gccaatatca tactgaatgg gcaaaaactg    2640
gaagcattcc ctttgaaaac tggcacaaga cagggacgcc ctctctcacc actcctattt    2700
aacatagtgt tggaagttct ggccagggca atcaggcagg agaaggaaat aaagggtatt    2760
caattaggaa aagaggaagt caaagtgtcc ctgtttgcag atgacatgat tgtatatcta    2820
gaaaacccca acgtctcagc ccaaaatctc cttaagctga tagacaactt cagcaatatc    2880
tcaggataca aaatcaatgt gcaaaaatca caagcattct tatacaccaa taacagacaa    2940
acagagccaa atcgtgagtg aactcccatt cacaattgct tcaaagagaa taaaatacct    3000
atgaatccaa cttacaaggg acatgaagga cctcttcaag aagaactaca aaccactgct    3060
caatgaaata aaagaggata caaacaaatg gaagaacatt ccatgctcat gggtaggaag    3120
aatcagtact gtgaaaatgg ccatactgcc caaggtaatt tatagattca atgccatccc    3180
catcaagcta ccaatgactt tcttcacaga attggaaaaa gctactttaa agttcatatg    3240
gaacccaaaa agagcctgca ttgccaagtc aatcctaagc caaagaaaca agctggagg    3300
catcacgcta cctgacttca aactatacta caaggctaca gtaaccaaaa cagcatggta    3360
ctggtaccaa aacagagata tagatcaatg gaacagaaca gagccctcag aaagaatgct    3420
gcatatctac aaccatctga tctttgacaa acctgacaaa acaagaaat ggggaaagga    3480
ttccctattt aataaatggt gctgggaaaa ctggctagcc atatgtagaa agctgaaatt    3540
ggaccccttc cttacacctt atacaaaaat taattcaaga tggattaaag acttaaatgt    3600
tagacctgaa accataaaaa ccctagaaga aaacctaggc aataccattc aggacatagg    3660
catgggcaag gacttcatgt ctaaaacacc aaaagaaatg gcaacaaaag ccaaaatcga    3720
caaatgggat ctaattaaac taagagcttc ctgcacagca agagaaacta ccatcagagt    3780
```

```
aagcaggcaa cctacagaat gggagaaaat tttcacaacc tactcatctg ataaagggct    3840
aatatccaga atctacaatg aactcaaaca aatttacaag aaaaaaacaa acaacccccat   3900 caaaaagtgg gcgaaggaca tgaacagaca cttctcaaaa aagagacattt atgcagccaa   3960 aagacacatg aaaaaatgct catcatcact ggccatcaga gaaatgcaaa tcaaaaccac   4020
aatgagatac cacctcacac cagttagaat ggcgatcatt aaaaagtcag gaaacaacaa   4080
gtgctggaga ggatgtggag aaatcggaac acttttacac tgttggtggg actgtaaact   4140
agttcaacca ttgtggaagt cagtgtggca attcctcagg gatttagaac tagaaatacc   4200
atttgaccca gcaatcttat tactgggtaa atacccaaag gattataaat catgctgcta   4260
taaagacaca tgcacacgta tgtttattgt ggcacaattc acaatagcaa agacttggaa   4320
ccaacccaca tgtccaacaa tgatagactg gattaagaaa atgtggcaca tatacaccat   4380
ggaatactat gcagccataa aaaatgatga gttcatgtcc tttgtaggga catggatgaa   4440
gctgaaaacc atcattctca gcaaactatc acaaggacaa aaaaccaaa caccgcatgt    4500 cctcactcat aggtgggaat tgaacaatga aacacatgg acacaggaag gggaacatca    4560
cacactgggg cctgttgtgg ggttagggga gtggggaggg atagcattag gagatatacc   4620
taatgttaaa tgacgagtta atgggtgcag cacaccaaca tggcacatgt atacatatgt   4680
aactaacctg cacgttgtgc acatgtaccc caaaacttaa agtagaataa aaaaaaaaa    4740 gacagagacc ttatggcctg caaaggctaa atatttact atttggtttt ttacagaaaa    4800
agcttgtcct tctctggtct gtactcttct gcctccatcc ccactcccca ctccaccact   4860
agattttttt cttttcttg agatagagtc tcactgtgtt gcccaggctg gagtgcagtg    4920
gcatgatctt ggctcactgc aacctcctgg gttcaagtga ttctcccacc tcagcttcct   4980
gagtaactag gactacaggt gcgagccata atgcccagct aattttgta ttttagtag     5040 agacggggtt tcaccgtgtt ggccaggctg gtctcgaact tctgacctca ggtgatccac   5100
ctgcctcggc ctctcgaagt actgggatta cagccactgc tgccggcaaa ttttttttta   5160
agcaaattac agataccata tcatttaatc cagtaacact tcagcatatt taatccaata   5220
gtacttcaga atatagtcat gtaaaagatg atgactcttt ctgcaaaact taatcagaat   5280
acatgattgt aacggaaaaa aaaaagaata gtaattcttt aataacatcc aatatccagt   5340
caacgtagag aggggggaact tggctctggg caacgtttcc actctcaacc cccgcaggcg   5400
tagtttctct ctccttccca ctgccacctc agtcctgtcc acaaactcca aaagggaaga   5460
ggtgggggaa gccttgctga gggagagcac gttttcccca ttctccaacc gtggcgacct   5520
gtgaccctct ttgaaactga gacaaatacc tgtgcatttg gcagccaaag cattgtgaca   5580
aacattgtgc acgtctatta tgagcccacc ctggctcctc cagggcccgc agcgtctgct   5640
ctgagctcct ctacctgatt tcaagactgg cacgtgtggc cctacattga tctctagact   5700 tttctgctc tgatcccttc cctgcttctt caagtcctcc agataggagt ctaagtcctt    5760
gatacccacc atgctcaaag acctcaggta aatatgccca ctctcctctt cctgcccacc   5820
cagtccatca aagcccattg gcaccaaagc cttctctcat ctgttcagcc gagggggtc    5880 tctcactctc cgaattctgt ttccattttt catcagaacc acgcagttta gtgtttcaga   5940
atttcaaacc taatacattc ccaatttgat ttataagctc ttcaaaggca ggaacttgtc   6000
ttatatttag cgccctcccc ctgccccac atccccatat acatgccatc cccaaaagtc    6060
tgttagtgac ttaaagtttc agaagtctag acatttgctc ttctcttttt tctcccttaa   6120
aatcacttgg aagtttgaag aggacatcat agacatctgc tttgagatcc tgaacaagag   6180
```

-continued

```
cctgtatcac ttaaagaacc cggccaaaga ctgttcccag cggaacgacg tggtgtatgt    6240
gtgcagggtg gtgagtgcca tggtaaggat ggatgcttcc cgccgtctga ggacagtctg    6300
agcttccccg ggagctgtgg aaacccacct gtctgtcctc tgcagatcaa cagcaacgat    6360
gacaatggcg tgctgcaggg gaactggggc gaggactact ccaaaggggt cagtcctctg    6420
gagtggaagg gcagcgtggc catcctacag cagtggtcag ccaggggcgg gcagcctgtg    6480
aagtacggac agtgctgggt cttcgcctct gttatgtgca ccggtgagcg aaagatcact    6540
cacttagggg tgtgattaac ttcattatca gagaagttaa ctgtggctca taaaggttca    6600
gtagcttgcc catggcccca cagctggggg tggtgggcac ccaggccctg agctagcaca    6660
ccatacagtc tcgagggatc ctgtgcattt atgtgagagg gggattgacc tgtggcaatc    6720
atctcacagt atccttgatg gatcagtcag actgttaaaa ctgtcatctg gatagaggag    6780
tttgtggtcc cgaagcagaa accaaatggc tcctttctgc cacctgctca ggcatctcag    6840
ctcagggtga gcctggcatg gggggcaggt ggaagtaga tggcgtgaga tagctgacct    6900
cacccatagg cagagctagc agcccccaaa tgcttcactg agagatcctt gagcagttat    6960
cattatagac ttgccacctt gctgactacc cttaaagaac atcaatgttt tatgcagtat    7020
caattattta caattcagtg caaagttgtt gagcagacca tctgtgaaga tgagagaaag    7080
atggagagta cttgtctcac ccttgcaagg ccagaatctg ttagacaggc ctgtcctgct    7140
acattatgga gctcgatgaa catttgctga actaacaggg tgactctgag ttggagaaag    7200
gaggagcaga gaatggggag gacagagaca ggtgccaaag acaagggcag agactttttg    7260
gagaggggca gcagaggctg gcagttatat acaggtgctg cagacacaga ggaggtttaa    7320
atctgagtgt ttgaatccag tgacctcact ttgcccaggt gtgaaatggg gctagggcta    7380
ccctggcact cagtattctc agttgttcct tgggctggga agtccccagg ccgtgctagg    7440
taggtgttat ggaggaggcc tgggatgagc aggagaagga cgaggtccac caccctgctc    7500
catttccaag cctctcccca ctcccaggcg ctcgagttac agggccactg cgcactgggg    7560
gagctgcccc tgccaagctt cctatggcca cttccagccc aggtgtagct cccacgcctg    7620
ctaaggatct gtgacaagcc caggagctgt gctgtgagtg gacaggtgac tgcagacagg    7680
aagccttctt gggggctctt cagtgaacca aaacaaaagg attggtcgct gtcaatattc    7740 ctttttacttt ttgaagctgt gtaatcctcc tggcagcctc agtaggcacc gtctgcccct    7800
cctaggaggg agatagtggg ataaacctct ctgaacttac catgctggct gatgtcagta    7860
cccacgtccc ctcagggtca cacctggctc ttgctggctc ttggcttgac ttcatctggc    7920
tctgggcagg caggggtgtg tgtgtgtgtg tgtgtttgtg tgtatgtgtt ggggtaatg     7980 tttacactgt gtgactagat ttgtgaaatc ataactcagc ttttaaaagc ctttgtagca    8040
gtatcatgag aagccacaag agggagctgc tgccttatta aagatggttg ctgactgtga    8100
tttcctctta tctctgctga cggtttccac tgtctctaga agtctatctt gtccctctat    8160
ccatcctcga atttctttca tacctccccc tacctcttgt ctttaagtag aattacagat    8220
cccaaatttc agagctaggg tgggaggagg gtgatgaaat aatctgtaca acaaccccc    8280 gtgacacgtg tttacccacg taacaaacct tcatgtgtac cctcaaacct aaaataaaag    8340
ttaaaaaaca tttcggaact aaattttcag cctccctagt agctggaact gcaggcatgc    8400
accaccacac ccagctaatt tttttttgta tttttagtag agacgggagtt tccccatgtt    8460 ggccaggctg agtctcaaac ccctgacctc gtgatccgcc tcagcctccc aaagtgctgg    8520
```

```
gattacaggc gtaagccacc gcgcctggcc ctctgtcttt aacttggaaa gctgctgagt    8580
ggaaagactc ctaaatgata agtcggatta ttgttaactg ttgttttaag cgaccctcaa    8640
atgattcctt tctccttgtg ggatgttgat cactgatggg gcagcagggc tgtgggactg    8700 ggtgtgggc tctgggaata aaggagttac tggtgtggtt ccgtaagcgt cttggctttc     8760
tctcctccag cttgaaagtt acaaattatg catggaaaac caataattct gcctgaaatg    8820
aactcagcga ttctctatat ttttctcttt agtaatgaga tgcttaggtg ttccaacccg    8880
tgttgtttcc aatttccgtt ccgcgcacaa cgtggatagg aacttgacca tcgatacgta    8940
ctatgaccga aatgccgaga tgctgtcaac tcagaaacga gacaaaatat ggtgagaggc    9000
actgtcttga acagatctct gctttgtccc agggagggca gaaaaactga cctggttctc    9060
tctggctctt gaggaaatat tgcaagattg ccctgagcat tgctgctaat gctcagagaa    9120
gagaagaatt ccccaaccca ggaggctgtt ctggctaatt aggtcatcaa atttaactca    9180
tttcagaggt agaaaacaat gggataacat tctggggcct caaccaaatg actagctggg    9240
cgtcttctga acactgacct caaagtctt tattcatctt cctctttctt ctctgagttt      9300
ctgtttgtac catccagttt tcccagaagt cagacagagc ctggactggc tgcttctgta    9360
gacctcttct tgtctctctt gacttcttcc tctgcccaac ccactccctg tctgcatgca    9420
tgtgtctgtg catgtatatg catgcgtgtg tgtgtgtgtg tgtatctctg tgcatcccctt    9480 tatttgtgta tctctggctt cttttcctgg ttcctttgtt ctcagctcta cccgcaaatc     9540
tggtttcctg tttctctttt tccagccagt ttccagataa gactcgctgt gttggtttgt    9600 ttgttttga gatggagtct cgctctgttg cccaggctgg agtgcaatgg tgcgaactca     9660
gctcactgca atctccacct cccaggttca agcaattctc ctgcctcagc cccccgagta   9720
gatgggacta caggcacgta ccaccacacc tggctaattt ttgtattttt agtagagacg    9780
gggtttcacc atgttggtct cgaactcttg acctcagatg atccactcgc ctcggcctcc    9840
caaagtgctg ggattacagg cctgagccac cgcacccagc ctccaggtaa gattccttga    9900
gttgtgtaag aactacctgc tgtcctagga gcccccctccg tctctgagct tcaatttcct    9960
tgtctgtaaa atgaagataa catctacttc acagggttgc tagggtgaaa tgagatcaat    10020
gccagtaagg agggcttttc agcctgggat ccacagatag actcctagag gtctgaattg    10080
tctctgattc aggaagcagt ggtgtatctg aggatatgta acttaggcac agttctgtct    10140
ttgaatgcat atcttgagtc taatcatgag gaaacatcag acaagcccaa aatgggggcc    10200
actctggttt taaaaaatag ataaataaca taaagactgt tttcattaaa agcccagact    10260
tcaccactag gtaatatctc catgaaacaa aactacattt gtaccctta catttacaaa      10320 aaaaagaaaa agagagagag cgagagattg ttttcaaatc ccaatgtaac aaagaaagac   10380
aggcgaagga actgttccaa gatcaaagga gacaacattc tgcgtagctg aatgcagtgt    10440
gtgatcacag acggcatcgc gtaccacatg ggagaagaat gctctaaaca acatcattag    10500
gtcaactgac aacattaaaa tatagacagt aaattagata aaggcatcat atcaatatcc    10560
aatgtgctag ggtttatgaa ctatacaggg gttatgtaag agaagatccc tattctcagg    10620
aaatacacac tgaagtgtgt atgtgtagat atctattcct gtccacactg aaagaaagca    10680 tatgggcaa aatgttaaca acagatgaat tgggtagatg ggtgttcttt gtactactct        10740 ttttttgttgt tttttttgaga tggagtctca ctctgtggcc caggctggag tgcagcggtg    10800
ccatcttggc tcactgcaag ctccgcctcc tgggttcaca ccattctcct gcctcagcct      10860
cccgagtagc tgggactaca ggtgcccgcc accatgccca gctactttt tgtattttg       10920
```

-continued

```
gtagagacag ggtttcactg tgttagccag gatggtctca atctcctgac ctcgtgatcc   10980
gcccacttcg gcttcccaaa gtgctgggat tacaggcgtg agtcaccgcg cccagcctgt   11040
actattcttg tgacttttag tatgaaatta cttcctaata aaaagtaaga aaaagaaaca   11100
atgatataaa tcactccgta tagtgcctgg tacctggcaa aacctcagct aacatgaatc   11160
cttgtctcct tactccctcc tgcaggaact tccacgtctg gaatgagtgc tgatgatcc    11220
ggaaagatct cccaccagga tacaacgggt ggcaggttct ggaccccact ccccagcaga   11280
ccagcagtgg tgagtgagga ccattgcaac aggctctggc tctgtgggga ggcagattag   11340
ggtgactggc cgtgggagca ggagaccagg gaggagcagc gttttccacg gcaccctctt   11400
cccgaggtcc cagctgacac agcttcagat caggaatcta actctaccat tgacagagtc   11460
acccggatgg gttacctgga tgggtcactg agcctcagtt gtgtccttac ctgtaaagtg   11520
gaaaagctga tgatgagcat tgccacttca cagggtggct gtgagggtca gatgaattaa   11580
tgggaacaaa agtgcttggt aaactggaag atatcccacg ggtgagagtc agtggtgccg   11640
ctgcctatcc catctccacc tcccacagcc acaaccagct gccctggcc cccatatcag   11700
tagcctgttg cctccacagg gctgttctgc tgtggccctg cctctgtgaa ggccatcagg   11760
gaagggatg tccacctggc ctatgacacc cctttgtgt atgccgaggt gaacgccgat    11820
gaagtcattt ggctccttgg ggatggccag gcccaggaaa tcctggccca caacaccagt   11880
tccatcggga aggagatcag cactaagatg gtgggtcag accagcgcca gagcatcacc    11940
agctcctaca agtacccaga aggtgctggg cgggtatttg gggaaagggc tgctttaagc   12000
ttctttgtga tgcttcctag ctgggatggc tccaagttga aaccatcacc atcgaatcac   12060
ctcttcctca tggcaaactc ctaggggtcc ttcctggatc ccaggcatgt ggccctaggg   12120
tagggttacc agcaaataaa aatacaggat gcccagttaa atttgaattc caggtagatc   12180
cagataaaca aatatttttat ttgtgtaata tatgtcccaa atgttgtatg agacatactt   12240
attctaaaaa gtattcactg tttatctgaa attcacactg gtatgatttt taatatata    12300
agtatgttcc aaatagtgca tgggatgtac tatactaaaa ataatttgtt gtttatctgg   12360
aatttaaatg tggttggatg tcctgtattt taactccacc cagagtggca ccaccgtctc    12420
cctatgtcca tggcaagggg agcggtggag tcaggggat gggcccctgg gcctgtggat     12480
ggggtggaca ccccacgga gggcgcatgt gtggagtcag gctgcctgag tactgaacag    12540
ggctctgcca tgccctgtgt aagactggac acagattacc actcctgtgc ctccatttcc   12600
tcatctgtaa aatgggataa cagtccctcg gacggctgtt gagaggttaa atgagtgtcc   12660
atagaaagca ctgggaacag tgcctgtgga atgcagcaac tgctccagag aagtccacag   12720
gtgggggtaa gtttgggtta agctgttgga ggcggcacaa atgtttctta tgattaggca   12780
taactgaagc ctgtcagtaa caatctgaac ctgtgctcaa ttaagcagct gaccagtcat   12840
tacctcctcc tccttgctct tgctacccaa ataaatatga agggcggtag acactcagcg   12900
gctgcctttg ctcactagaa gcagggagcc ctttcttctt ctcttctttt ccccttctct   12960
tttcttattc cgcatgctag cctttcctta aaacagtttc ttctgttttt taccatttct   13020
acattcatcc cttcgttcag tcttgtaatg atggtctcaa gtagtaacag tagtaactgt   13080
ggtaatgatg gtctcaagta gtagcagtgg cagccagcca cattaagcct ccatgttaag   13140
tagcccccat gggcaagaga tgaagctctt ttgtttttttt tttaggcgga gtttcactct   13200
tgttgcccag gctggagtgc aatggcgcaa tctcggctca ctgcaacctc cacctcctgg   13260
```

```
gttcaagcta ttctcctgcc tcaccctcct gaatagctgg gattacgggc acccatcacc  13320
atgcccagct aattttgta ttttagtaga gacgaggttt cactatgttg gccagtctgg   13380
tctcaaactc ctgacctcag gcgatccacc catctcaacc tcccaaattg ctgggattac   13440
aggcgtgagc cactgcgcct ggccgaagct cttttttatg tttcgagcat atatcttagc   13500
tggagggatg ctggtagggg agagaagcct ctggcttcat gatgatgatg atagtgatgc   13560
tggtggccat agtgatggta gaaaacagtg ctgagtcctt gcagccagca actcagcctg   13620
acgttttgg gatcccttat aaggaaagca gatatcatcc ccaggttaca gatgacagaa    13680
cagaacactg agagattaaa ggactgtgac agagcaagga tttgaaccca gcaagcagca   13740
cctgagccgc gccgcctccc tgtgctgcta ttcctgtgcc ttgttgcccc aggaaagtca   13800
ctggtcctct ccaccctcc ccatgcatgt ctctcctacc tctcccttct gcaggatccc    13860
ctgaggagag agctgtcttc atgaaggctt ctcggaaaat gctgggcccc caaagagctt   13920
cttttgccctt cctggatctc ctggagtctg ggggtcttag ggatcagcca gcgcagctgc  13980
agcttcacct ggccaggata cccgagtggg gccaggacct gcagctgctg ctgcgtatcc   14040
agagggtgcc agacagcacc cccctcgg ggcccatcgg actggtggtg cgcttctgtg     14100
cacaggccct gctgcatggg ggtggtaccc agaagccctt ctggaggcac acagtgcgga   14160
tgaacctgga ctttgggaag ggtgagtgtg aggcaggcct gagaaggcac ctacaggag    14220
gggagctgtg ggtccatgaa cacagtgggg tgggcccagc cagattacac acagacccct   14280
tcctccaaca cacacacatt ctgggcagtg aagctgccag ctgctgcacc tctgatgcca   14340
ccccaccagg cgagacggag cagtgagccc tggggacagt gtgtgcgtgg tgggacgctg   14400
tctgtctgtc tctcacacac acttttacct ctcacgtgaa aattctaatt tttcctctct   14460
cacatctaca tgtcccccct ctctctggtc catgtcctgg actcaaggtg tcttttgtat   14520
gtgcttagag acacagtggc cgctcctcct gccctacagc aattacagaa acaagctaac   14580
ggacgaaaag ctcatccgcg tgtctggcat cgccgaggtt gaagagacag ggaggtccat   14640
gctggtccta aaagatatct gtctggagcc tccccacttg tctattgagg tagtgtctgg   14700
acatgggtgg gggctctgag gctctctgac tcacccaatc caggggctgg ggtgcagcag   14760
ccaacaagac actgttccca cctcacacca caccgatggc tccagcacag tatggtgtgg   14820
tctagtgctc tgtaccagcg tggggttgga ggggcatgaa ggcttctcaa aggacgtgct   14880
attttttcaga ggatgcatag gaaactatag agaaattaga tggccgtgaa ggcatttaa   14940
gtaaggaaat cattttgcaa aggcaaagag acgggaaagg cagtgactag gagatgaagt   15000
agaggagaca gatttagaga ctccacaaag tcaaattcaa acgatgacca ctggctaagc   15060
atggtggctc atgcctgtaa tcccagtgct ttgggaggcc aaggcgggag gatcacttga   15120
acccaggagt tcgagaccag tctgggcaac atagcgagac cttgcctcta cttaaaagtt   15180
tttcaaaagt tagctggtgt ggtggtgcat gcctctagtc ccagatactc aggaggctga   15240
ggtgggagtc cagggaaatc aagcctgcag tgagctgaga tcatgccact tcactccagc   15300
ctagacaaca gagtgagacc ttgtctcaac aaaacaaaac aaaaggtgag tattgacaag   15360
attgaggtga caaagacgga aacaaatgaa aagtgaactt cagattttga gttcagatgc   15420
ctgagtggcc agtgaggcca ttacacaaag aaggaatttc aggcaaagga agggtgaatg   15480
gaagagggca ggtgcattcc ccatctcctg ctaccagggt tttccttccc gaaagcctcg   15540
ttttctcacc tgcccctccc actcagaaag acttgcccac tgcctagtcc aaacctggct   15600
ctgtacctgg aggcttctcc aacagcctgc ccctcccac cccaatagag aactgggcag    15660
```

```
ctccagacca taaatcagct ggcctacccc agggttttca cccaggcaca ctgtcaggct   15720
gtcgggccag ctgacaccag gcagcctctg tgctggggca aacagtgggc agaactgcaa   15780
gtgcagacat aagcctgggg ctgtggccag ggccctgccg tgtacctgaa gcaaacatgg   15840
caaatgccaa gtaggttgct aattggtccc catcagtaag ggatctgcag atgattccac   15900
agttatttta acctgttcta cttttgacacc cttatgaggg tacaagggac ttggtatttt   15960
tgtttggacc ccaggtgagt caggtgtgtt cttccttttc cttgagtctc tggcccagcc   16020
agaacaagcc cctagtacga tctgggtggt cagagctcat ttcagttcaa cacgtgctta   16080
ctgatatcca tcatctggcc ggcactgttc taggcccagg ggctccagaa atgagtagga   16140
aggatgcctg cctcccactc acaggccaca gctgtgctgc cccgtgacac agcactgagc   16200
acacctggaa aaactcgagt gcatgccctg ctgatgttta tgaagacaca gcagcgtggg   16260
gaaagatcct aggctgggt ctgggacacc tgggtcaggt cctggctctg ccattaacac   16320
atcatgcagc cttggcctca ctgtttcctc ggtgatgagc gtaagggcag gatgacatca   16380
ctgatggcac atgggtggca cacgacacac cacttcctta tcccacacct gtgttagata   16440
tgaatcaatt gtgatccttt gtcctcagga tcctttaac acagccttcc tagtagccac   16500
ccactgagc tggcacttcc atttaaatct tgtggacatc ttgaactaga tggtggggac   16560
agaaagggt ttcagcttgg tggcaactgc tgattggtgg tggctccttg gagtattgtg   16620
acctaatgca ggcctgtata tgtgttaatc tcaagtactc tcagctcaca ttcctccctc   16680
gccactgtgg cacattagct ctaagccgca gttcctggtg gtcgccaggg acctgggggt   16740
gggggtaact gaaccagagt gcagaagcga ggccagttgc ccatgggatt gctgacttct   16800
ctccacacag gtgtctgaga gggctgaggt gggcaaggcg ctgagagtcc atgtcaccct   16860
caccaacacc ttaatggtgg ctctgagcag ctgcacgatg gtgctggaag gaagcggcct   16920
catcaatggg cagatagcaa aggagtaagt gacgcttctg cccacctccc ccttgctggt   16980
ctcaggaaag gggtgcccca tggcgtcaca ggaccctcct cagtctcctg tgcagtgcct   17040
ctctgccccc actttctcac cctcctcagg aaaggctgag ctcagtggtg gtggtgagtg   17100
ggagcctctt acccacccag aggggaacca gatcacccct gccgccagca ggaagtcctc   17160
gaggctctca caggctgttt ctgactttca gccttgggac tctggtgcc ggacacaccc   17220
tccaaattca actggacctc tacccgacca aagctggacc ccgccagctc caggttctca   17280
tcagcagcaa cgaggtcaag gagatcaaag gctacaagga catcttcgtc actgtggctg   17340
gggctccctg agaccccgcc tccagctgcc ctccctggca cccctgcccc acctggctcc   17400
tttctactcc tggctatgtc gtcttggctc cacctctgtc ctctctctag cctgcctggg   17460
aatgaatgaa gctctgttag aaacaccgtg tgctttggga agagacaata aagatgtctt   17520
tatttatcac cagcattctc aagccactta ttgctcctgg ctgatcctct tggcctggct   17580
gccagctctg tggctgaacc ctcccttccc ctcctgtcct ctctctcctc ccttaagagc   17640
ctcaaccaca aaataagccc accaccatcc cctctaaagc agcctctctg gaattaagga   17700
tcccaggtct ctccatttac attgtcttag tgagcctgca ggcagaggat ggagggaggc   17760
ctggggaggg cggtttggat gtgccggag acagcaacc ctgtggcaac tggccagaag   17820
ctgcccagca ggactgttct gcccccagcc tagagtatcc tgggaggcac aggcagccac   17880
cttttccgcat gcgttcattg acagacagga tgactgggaa gcgctgcata gctggctgct   17940
gtctagcaac agcctcacct gctatccctg tccccgccct tgcctctcgc tccctcaccc   18000
```

-continued

```
tcatcttgca ttcttcccca tcatcccaac tctcagcctc tcttcctttg tgtggtattt  18060
gtttgtttgt ttgtttgttc ttttagacag agtttctctc ctgttgccca ggctggagtg  18120
caatggcgtg atcttggctt actgcaacct ccacctcctg ggttcaagcg attctcctgc  18180
cttagcctcc cgagtagctg ggattacagg cacgccacca tgctcggcta atttttttgt  18240
atttttagta gagtcggggtt ttccccatgt tggccaggct ggtctcgaac tcctgacctc  18300
aggtgatccg cctgcttcgg cctcccaaag tgctgggaat ataggcatag ccaccacgcc  18360
cggcctcctt tgtgtctttt gtttttgtta ttttaaggac agagggagcc actcttttgt  18420
atttctttct cctgtggtta ccaaaattac tcctgctcat tctagatgat ttggaaagtg  18480
gaaaaaaaaa aaaaaaaact aacgaaagga aaatcaccaa tagctccccc atcccagaga  18540
aaatccttgc taacatttct caagagatca ttctggcttt cagccttggg actctggtgg  18600
ctggacacac catccaattt cctttatttc cccttttatt atgttgttga aaagtcagca  18660
ttacaaatgg atacatctcc atcatagata atttagaaaa ttcagaaaca tgggaaagga  18720
gagcatcttc ctgtcagtct gcaggcacat ccactcctca cctgctccgc ggctctatag  18780
ttttgacttc tttcagtctt cccttccctt cccctcctcc tctccctctt tctctccctc  18840
ttcttcctcc tcttctccct tttcctccct tttcctgctc tccttcctcc tcttccccct  18900
ccctctcttc tctgtatttt tttgtttgcc cctagtcctc cttctccttc ccttctattt  18960
tctctctctc tctctctctt tttttttttt tttttttttt                        19000
```

<210> SEQ ID NO 4
<211> LENGTH: 2112
<212> TYPE: DNA
<213> ORGANISM: Artificial Sequence
<220> FEATURE:
<223> OTHER INFORMATION: degenerate sequence
<221> NAME/KEY: misc_feature
<222> LOCATION: (1)...(2112)
<223> OTHER INFORMATION: n = A,T,C or G

<400> SEQUENCE: 4

```
ytnmgnytng arwsngtnga yytncarwsn wsnmgnaaya ayaargarca ycayacncar    60
garatgggng tnaarmgnyt nacngtnmgn mgnggncarc cnttytayyt nmgnytnwsn   120
ttywsnmgnc cnttycarws ncaraaygay cayathacnt tygtngcnga racnggnccn   180
aarccnwsng arytnytngg nacnmgngcn acnttyttyy tnacnmgngt ncarccnggn   240
aaygtntggw sngcnwsnga yttyacnath gaywsnaayw snytncargt nwsnytntty   300
acnccngcna aygcngtnat hggncaytay acnytnaara thgarathws ncarggncar   360
ggncaywsng tnacntaycc nytnggnacn ttyathytny tnttyaaycc ntggwsnccn   420
gargaygayg tntayytncc nwsngarath ytnytncarg artayathat gmgngaytay   480
ggnttygtnt ayaarggnca ygarmgntty athacnwsnt ggccntggaa ytayggncar   540
ttygargarg ayathathga yathtgytty garathytna ayaarwsnyt ntaycayytn   600
aaraayccng cnaargaytg ywsncarmgn aaygaygtng tntaygtntg ymgngtngtn   660
wsngcnatga thaaywsnaa ygaygayaay ggngtnytnc arggnaaytg gggngargay   720
taywsnaarg gngtnwsncc nytngartgg aarggnwsng tngcnathyt ncarcartgg   780
wsngcnmgng gnggncarcc ngtnaartay ggncartgyt gggtnttygc nwsngtnatg   840
tgyacngtna tgmgntgyyt nggngtnccn acnmgngtng tnwsnaaytt ymgnwsngcn   900
cayaaygtng aymgnaayyt nacnathgay acntaytayg aymgnaaygc ngaratgytn   960
```

-continued

```
wsnacncara armgngayaa rathtggaay ttycaygtnt ggaaygartg ytggatgath   1020
mgnaargayy tnccnccngg ntayaayggn tggcargtny tngayccnac nccncarcar   1080
acnwsnwsng gnytnttytg ytgyggnccn gcnwsngtna argcnathmg ngarggngay   1140
gtncayytng cntaygayac nccnttygtn taygcngarg tnaaygcnga ygargtnath   1200
tggytnytng gngayggnca rgcncargar athytngcnc ayaayacnws nwsnathggn   1260
aargarathw snacnaarat ggtnggnwsn gaycarmgnc arwsnathac nwsnwsntay   1320
aartayccng arggnwsncc ngargarmgn gcngtnttya tgaargcnws nmgnaaratg   1380
ytnggnccnc armgngcnws nytnccntty ytngayytny tngarwsngg nggnytnmgn   1440
gaycarccng cncarytnca rytncayytn gcnmgnathc cngartgggg ncargayytn   1500
carytnytny tnmgnathca rmgngtnccn gaywsnacnc ayccnmgngg nccnathggn   1560
ytngtngtnm gnttytgygc ncargcnytn ytncayggng gnggnacnca raarccntty   1620
tggmgncaya cngtnmgnat gaayytngay ttyggnaarg aracncartg gccnytnytn   1680
ytnccntayw snaaytaymg naayaarytn acngaygara arytnathmg ngtnwsnggn   1740
athgcngarg tngargarac nggnmgnwsn atgytngtny tnaargayat htgyytngar   1800
ccnccncayy tnwsnathga rgtnwsngar mgngcngarg tnggnaargc nytnmgngtn   1860
caygtnacny tnacnaayac nytnatggtn gcnytnwsnw sntgyacnat ggtnytngar   1920
ggnwsnggny tnathaaygg ncarathgcn aargayytng gnacnytngt ngcnggncay   1980
acnytncara thcarytnga yytntayccn acnaargcng gnccnmgnca rytncargtn   2040
ytnathwsnw snaaygargt naargarath aarggntaya argayathtt ygtnacngtn   2100
gcnggngcnc cn                                                       2112
```

<210> SEQ ID NO 5
<211> LENGTH: 6
<212> TYPE: PRT
<213> ORGANISM: Artificial Sequence
<220> FEATURE:
<223> OTHER INFORMATION: peptide tag

<400> SEQUENCE: 5

```
Glu Tyr Met Pro Met Glu
 1               5
```

<210> SEQ ID NO 6
<211> LENGTH: 2308
<212> TYPE: DNA
<213> ORGANISM: Homo sapiens
<220> FEATURE:
<221> NAME/KEY: CDS
<222> LOCATION: (1)...(2133)

<400> SEQUENCE: 6

```
atg gat cag gtg gca acc ttg cgg ctt gag tct gtc gac ctg cag agc       48
Met Asp Gln Val Ala Thr Leu Arg Leu Glu Ser Val Asp Leu Gln Ser
 1               5                  10                  15 tcc agg aac aac aag gag cac cac acg cag gag atg ggc gtc aag cgg       96
Ser Arg Asn Asn Lys Glu His His Thr Gln Glu Met Gly Val Lys Arg
            20                  25                  30 ctc act gtg cgc cgc ggc cag ccc ttc tac ctc cgg ctg agc ttc agc      144
Leu Thr Val Arg Arg Gly Gln Pro Phe Tyr Leu Arg Leu Ser Phe Ser
        35                  40                  45 cga ccc ttc cag tcc cag aac gac cac atc acc ttt gtg gct gag acc      192
Arg Pro Phe Gln Ser Gln Asn Asp His Ile Thr Phe Val Ala Glu Thr
    50                  55                  60
```

-continued

| | | |
|---|---|---|
| gga ccc aag ccg tca gag ctg ctg ggg acc cga gcc aca ttc ttc ctc<br>Gly Pro Lys Pro Ser Glu Leu Leu Gly Thr Arg Ala Thr Phe Phe Leu<br>65                      70                      75                      80 | 240 |
| acc cgg gtc cag ccc ggg aat gtc tgg agc gct tct gat ttc acc att<br>Thr Arg Val Gln Pro Gly Asn Val Trp Ser Ala Ser Asp Phe Thr Ile<br>                      85                      90                      95 | 288 |
| gac tcc aac tct ctc caa gtt tcc ctt ttc aca cca gcc aat gca gtt<br>Asp Ser Asn Ser Leu Gln Val Ser Leu Phe Thr Pro Ala Asn Ala Val<br>                  100                    105                    110 | 336 |
| att ggc cat tac act ctg aaa ata gag atc tct cag ggc caa ggt cac<br>Ile Gly His Tyr Thr Leu Lys Ile Glu Ile Ser Gln Gly Gln Gly His<br>            115                    120                    125 | 384 |
| agt gtg act tac ccg ctg gga act ttc atc cta ctt ttt aac cct tgg<br>Ser Val Thr Tyr Pro Leu Gly Thr Phe Ile Leu Leu Phe Asn Pro Trp<br>130                      135                    140 | 432 |
| agt cca gag gac gac gtc tac ctg cca agt gaa ata ctg ctg cag gag<br>Ser Pro Glu Asp Asp Val Tyr Leu Pro Ser Glu Ile Leu Leu Gln Glu<br>145                      150                    155                    160 | 480 |
| tat atc atg cga gat tat ggc ttt gtt tac aag ggt cat gaa aga ttc<br>Tyr Ile Met Arg Asp Tyr Gly Phe Val Tyr Lys Gly His Glu Arg Phe<br>                  165                    170                    175 | 528 |
| atc acc tcc tgg ccc tgg aac tac ggg cag ttt gaa gag gac atc ata<br>Ile Thr Ser Trp Pro Trp Asn Tyr Gly Gln Phe Glu Glu Asp Ile Ile<br>            180                    185                    190 | 576 |
| gac atc tgc ttt gag atc ctg aac aag agc ctg tat cac tta aag aac<br>Asp Ile Cys Phe Glu Ile Leu Asn Lys Ser Leu Tyr His Leu Lys Asn<br>              195                    200                    205 | 624 |
| ccg gcc aaa gac tgt tcc cag cgg aac gac gtg gtg tat gtg tgc agg<br>Pro Ala Lys Asp Cys Ser Gln Arg Asn Asp Val Val Tyr Val Cys Arg<br>210                      215                    220 | 672 |
| gtg gtg agt gcc atg atc aac agc aac gat gac aat ggc gtg ctg cag<br>Val Val Ser Ala Met Ile Asn Ser Asn Asp Asp Asn Gly Val Leu Gln<br>225                      230                    235                    240 | 720 |
| ggg aac tgg ggc gag gac tac tcc aaa ggg gtc agt cct ctg gag tgg<br>Gly Asn Trp Gly Glu Asp Tyr Ser Lys Gly Val Ser Pro Leu Glu Trp<br>                  245                    250                    255 | 768 |
| aag ggc agc gtg gcc atc cta cag cag tgg tca gcc agg ggc ggg cag<br>Lys Gly Ser Val Ala Ile Leu Gln Gln Trp Ser Ala Arg Gly Gly Gln<br>            260                    265                    270 | 816 |
| cct gtg aag tac gga cag tgc tgg gtc ttc gcc tct gtt atg tgc acc<br>Pro Val Lys Tyr Gly Gln Cys Trp Val Phe Ala Ser Val Met Cys Thr<br>              275                    280                    285 | 864 |
| gta atg aga tgc tta ggt gtt cca acc cgt gtt gtt tcc aat ttc cgt<br>Val Met Arg Cys Leu Gly Val Pro Thr Arg Val Val Ser Asn Phe Arg<br>            290                    295                    300 | 912 |
| tcc gcg cac aac gtg gat agg aac ttg acc atc gat acg tac tat gac<br>Ser Ala His Asn Val Asp Arg Asn Leu Thr Ile Asp Thr Tyr Tyr Asp<br>305                      310                    315                    320 | 960 |
| cga aat gcc gag atg ctg tca act cag aaa cga gac aaa ata tgg aac<br>Arg Asn Ala Glu Met Leu Ser Thr Gln Lys Arg Asp Lys Ile Trp Asn<br>                  325                    330                    335 | 1008 |
| ttc cac gtc tgg aat gag tgc tgg atg atc cgg aaa gat ctc cca cca<br>Phe His Val Trp Asn Glu Cys Trp Met Ile Arg Lys Asp Leu Pro Pro<br>              340                    345                    350 | 1056 |
| gga tac aac ggg tgg cag gtt ctg gac ccc act ccc cag cag acc agc<br>Gly Tyr Asn Gly Trp Gln Val Leu Asp Pro Thr Pro Gln Gln Thr Ser<br>            355                    360                    365 | 1104 |
| agt ggg ctg ttc tgc tgt ggc cct gcc tct gtg aag gcc atc agg gaa<br>Ser Gly Leu Phe Cys Cys Gly Pro Ala Ser Val Lys Ala Ile Arg Glu | 1152 |

-continued

|  |  |  |  |
|---|---|---|---|
| 370 | 375 | 380 | |
| ggg gat gtc cac ctg gcc tat gac acc cct ttt gtg tat gcc gag gtg<br>Gly Asp Val His Leu Ala Tyr Asp Thr Pro Phe Val Tyr Ala Glu Val<br>385                           390                      395                   400 | 1200 | |
| aac gcc gat gaa gtc att tgg ctc ctt ggg gat ggc cag gcc cag gaa<br>Asn Ala Asp Glu Val Ile Trp Leu Leu Gly Asp Gly Gln Ala Gln Glu<br>                        405                      410                      415 | 1248 | |
| atc ctg gcc cac aac acc agt tcc atc ggg aag gag atc agc act aag<br>Ile Leu Ala His Asn Thr Ser Ser Ile Gly Lys Glu Ile Ser Thr Lys<br>                420                      425                      430 | 1296 | |
| atg gtg ggg tca gac cag cgc cag agc atc acc agc tcc tac aag tac<br>Met Val Gly Ser Asp Gln Arg Gln Ser Ile Thr Ser Ser Tyr Lys Tyr<br>         435                      440                      445 | 1344 | |
| cca gaa gga tcc cct gag gag aga gct gtc ttc atg aag gct tct cgg<br>Pro Glu Gly Ser Pro Glu Glu Arg Ala Val Phe Met Lys Ala Ser Arg<br>450                           455                      460 | 1392 | |
| aaa atg ctg ggc ccc caa aga gct tct ttg ccc ttc ctg gat ctc ctg<br>Lys Met Leu Gly Pro Gln Arg Ala Ser Leu Pro Phe Leu Asp Leu Leu<br>465                         470                      475                   480 | 1440 | |
| gag tct ggg ggt ctt agg gat cag cca gcg cag ctg cag ctt cac ctg<br>Glu Ser Gly Gly Leu Arg Asp Gln Pro Ala Gln Leu Gln Leu His Leu<br>               485                      490                      495 | 1488 | |
| gcc agg ata ccc gag tgg ggc cag gac ctg cag ctg ctg cgt atc<br>Ala Arg Ile Pro Glu Trp Gly Gln Asp Leu Gln Leu Leu Arg Ile<br>         500                      505                      510 | 1536 | |
| cag agg gtg cca gac agc acc cac cct cgg ggg ccc atc gga ctg gtg<br>Gln Arg Val Pro Asp Ser Thr His Pro Arg Gly Pro Ile Gly Leu Val<br>               515                      520                      525 | 1584 | |
| gtg cgc ttc tgt gca cag gcc ctg ctg cat ggg ggt ggt acc cag aag<br>Val Arg Phe Cys Ala Gln Ala Leu Leu His Gly Gly Gly Thr Gln Lys<br>530                           535                      540 | 1632 | |
| ccc ttc tgg agg cac aca gtg cgg atg aac ctg gac ttt ggg aag gag<br>Pro Phe Trp Arg His Thr Val Arg Met Asn Leu Asp Phe Gly Lys Glu<br>545                           550                      555                   560 | 1680 | |
| aca cag tgg ccg ctc ctc ctg ccc tac agc aat tac aga aac aag cta<br>Thr Gln Trp Pro Leu Leu Leu Pro Tyr Ser Asn Tyr Arg Asn Lys Leu<br>                       565                      570                      575 | 1728 | |
| acg gac gaa aag ctc atc cgc gtg tct ggc atc gcc gag gtt gaa gag<br>Thr Asp Glu Lys Leu Ile Arg Val Ser Gly Ile Ala Glu Val Glu Glu<br>               580                      585                      590 | 1776 | |
| aca ggg agg tcc atg ctg gtc cta aaa gat atc tgt ctg gag cct ccc<br>Thr Gly Arg Ser Met Leu Val Leu Lys Asp Ile Cys Leu Glu Pro Pro<br>         595                      600                      605 | 1824 | |
| cac ttg tct att gag gtg tct gag agg gct gag gtg ggc aag gcg ctg<br>His Leu Ser Ile Glu Val Ser Glu Arg Ala Glu Val Gly Lys Ala Leu<br>610                           615                      620 | 1872 | |
| aga gtc cat gtc acc ctc acc aac acc tta atg gtg gct ctg agc agc<br>Arg Val His Val Thr Leu Thr Asn Thr Leu Met Val Ala Leu Ser Ser<br>625                           630                      635                   640 | 1920 | |
| tgc acg atg gtg ctg gaa gga agc ggc ctc atc aat ggg cag ata gca<br>Cys Thr Met Val Leu Glu Gly Ser Gly Leu Ile Asn Gly Gln Ile Ala<br>                        645                      650                      655 | 1968 | |
| aag gac ctt ggg act ctg gtg gcc gga cac acc ctc caa att caa ctg<br>Lys Asp Leu Gly Thr Leu Val Ala Gly His Thr Leu Gln Ile Gln Leu<br>         660                      665                      670 | 2016 | |
| gac ctc tac ccg acc aaa gct gga ccc cgc cag ctc cag gtt ctc atc<br>Asp Leu Tyr Pro Thr Lys Ala Gly Pro Arg Gln Leu Gln Val Leu Ile<br>               675                      680                      685 | 2064 | |
| agc agc aac gag gtc aag gag atc aaa ggc tac aag gac atc ttc gtc | 2112 | |

```
Ser Ser Asn Glu Val Lys Glu Ile Lys Gly Tyr Lys Asp Ile Phe Val
    690                 695                 700 act gtg gct ggg gct ccc tga gacccgccct ccagctgccc tccctggcac      2163
Thr Val Ala Gly Ala Pro *
705                 710 ccctgcccca cctggctcct ttctactcct ggctatgtcg tcttggctcc acctctgtcc   2223
tctctctagc ctgcctggga atgaatgaag ctctgttaga aacaccgtgt gctttgggaa   2283
gagacaataa agatgtctttt attta                                        2308

<210> SEQ ID NO 7
<211> LENGTH: 710
<212> TYPE: PRT
<213> ORGANISM: Homo sapiens

<400> SEQUENCE: 7

Met Asp Gln Val Ala Thr Leu Arg Leu Glu Ser Val Asp Leu Gln Ser
1               5                   10                  15

Ser Arg Asn Asn Lys Glu His His Thr Gln Glu Met Gly Val Lys Arg
            20                  25                  30

Leu Thr Val Arg Arg Gly Gln Pro Phe Tyr Leu Arg Leu Ser Phe Ser
        35                  40                  45

Arg Pro Phe Gln Ser Gln Asn Asp His Ile Thr Phe Val Ala Glu Thr
    50                  55                  60

Gly Pro Lys Pro Ser Glu Leu Leu Gly Thr Arg Ala Thr Phe Phe Leu
65                  70                  75                  80

Thr Arg Val Gln Pro Gly Asn Val Trp Ser Ala Ser Asp Phe Thr Ile
                85                  90                  95

Asp Ser Asn Ser Leu Gln Val Ser Leu Phe Thr Pro Ala Asn Ala Val
            100                 105                 110

Ile Gly His Tyr Thr Leu Lys Ile Glu Ile Ser Gln Gly Gln Gly His
        115                 120                 125

Ser Val Thr Tyr Pro Leu Gly Thr Phe Ile Leu Leu Phe Asn Pro Trp
    130                 135                 140

Ser Pro Glu Asp Asp Val Tyr Leu Pro Ser Glu Ile Leu Leu Gln Glu
145                 150                 155                 160

Tyr Ile Met Arg Asp Tyr Gly Phe Val Tyr Lys Gly His Glu Arg Phe
                165                 170                 175

Ile Thr Ser Trp Pro Trp Asn Tyr Gly Gln Phe Glu Glu Asp Ile Ile
            180                 185                 190

Asp Ile Cys Phe Glu Ile Leu Asn Lys Ser Leu Tyr His Leu Lys Asn
        195                 200                 205

Pro Ala Lys Asp Cys Ser Gln Arg Asn Asp Val Val Tyr Val Cys Arg
    210                 215                 220

Val Val Ser Ala Met Ile Asn Ser Asn Asp Asn Gly Val Leu Gln
225                 230                 235                 240

Gly Asn Trp Gly Glu Asp Tyr Ser Lys Gly Val Ser Pro Leu Glu Trp
                245                 250                 255

Lys Gly Ser Val Ala Ile Leu Gln Gln Trp Ser Ala Arg Gly Gly Gln
            260                 265                 270

Pro Val Lys Tyr Gly Gln Cys Trp Val Phe Ala Ser Val Met Cys Thr
        275                 280                 285

Val Met Arg Cys Leu Gly Val Pro Thr Arg Val Val Ser Asn Phe Arg
    290                 295                 300

Ser Ala His Asn Val Asp Arg Asn Leu Thr Ile Asp Thr Tyr Tyr Asp
```

```
                305                 310                 315                 320
Arg Asn Ala Glu Met Leu Ser Thr Gln Lys Arg Asp Lys Ile Trp Asn
                    325                 330                 335
Phe His Val Trp Asn Glu Cys Trp Met Ile Arg Lys Asp Leu Pro Pro
                    340                 345                 350
Gly Tyr Asn Gly Trp Gln Val Leu Asp Pro Thr Pro Gln Gln Thr Ser
                    355                 360                 365
Ser Gly Leu Phe Cys Cys Gly Pro Ala Ser Val Lys Ala Ile Arg Glu
            370                 375                 380
Gly Asp Val His Leu Ala Tyr Asp Thr Pro Phe Val Tyr Ala Glu Val
385                 390                 395                 400
Asn Ala Asp Glu Val Ile Trp Leu Leu Gly Asp Gly Gln Ala Gln Glu
                405                 410                 415
Ile Leu Ala His Asn Thr Ser Ser Ile Gly Lys Glu Ile Ser Thr Lys
            420                 425                 430
Met Val Gly Ser Asp Gln Arg Gln Ser Ile Thr Ser Ser Tyr Lys Tyr
            435                 440                 445
Pro Glu Gly Ser Pro Glu Glu Arg Ala Val Phe Met Lys Ala Ser Arg
        450                 455                 460
Lys Met Leu Gly Pro Gln Arg Ala Ser Leu Pro Phe Leu Asp Leu Leu
465                 470                 475                 480
Glu Ser Gly Gly Leu Arg Asp Gln Pro Ala Gln Leu Gln Leu His Leu
                485                 490                 495
Ala Arg Ile Pro Glu Trp Gly Gln Asp Leu Gln Leu Leu Leu Arg Ile
            500                 505                 510
Gln Arg Val Pro Asp Ser Thr His Pro Arg Gly Pro Ile Gly Leu Val
            515                 520                 525
Val Arg Phe Cys Ala Gln Ala Leu Leu His Gly Gly Thr Gln Lys
        530                 535                 540
Pro Phe Trp Arg His Thr Val Arg Met Asn Leu Asp Phe Gly Lys Glu
545                 550                 555                 560
Thr Gln Trp Pro Leu Leu Leu Pro Tyr Ser Asn Tyr Arg Asn Lys Leu
                565                 570                 575
Thr Asp Glu Lys Leu Ile Arg Val Ser Gly Ile Ala Glu Val Glu Glu
            580                 585                 590
Thr Gly Arg Ser Met Leu Val Leu Lys Asp Ile Cys Leu Glu Pro Pro
            595                 600                 605
His Leu Ser Ile Glu Val Ser Glu Arg Ala Glu Val Gly Lys Ala Leu
        610                 615                 620
Arg Val His Val Thr Leu Thr Asn Thr Leu Met Val Ala Leu Ser Ser
625                 630                 635                 640
Cys Thr Met Val Leu Glu Gly Ser Gly Leu Ile Asn Gly Gln Ile Ala
                645                 650                 655
Lys Asp Leu Gly Thr Leu Val Ala Gly His Thr Leu Gln Ile Gln Leu
                660                 665                 670
Asp Leu Tyr Pro Thr Lys Ala Gly Pro Arg Gln Leu Gln Val Leu Ile
            675                 680                 685
Ser Ser Asn Glu Val Lys Glu Ile Lys Gly Tyr Lys Asp Ile Phe Val
        690                 695                 700
Thr Val Ala Gly Ala Pro
705                 710
```